United States Patent
Judy et al.

(10) Patent No.: US 11,990,704 B2
(45) Date of Patent: May 21, 2024

(54) RELIABLE MINIATURE IMPLANTABLE CONNECTOR WITH HIGH CHANNEL DENSITY AND METHODS OF USING THE SAME

(71) Applicant: UNIVERSITY OF FLORIDA RESEARCH FOUNDATION, INCORPORATED, Gainesville, FL (US)

(72) Inventors: Jack Judy, Gainesville, FL (US); Paritosh Rustogi, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 461 days.

(21) Appl. No.: 17/282,894

(22) PCT Filed: Oct. 4, 2019

(86) PCT No.: PCT/US2019/054765
§ 371 (c)(1),
(2) Date: Apr. 5, 2021

(87) PCT Pub. No.: WO2020/072941
PCT Pub. Date: Apr. 9, 2020

(65) Prior Publication Data
US 2021/0351544 A1 Nov. 11, 2021

Related U.S. Application Data

(60) Provisional application No. 62/882,302, filed on Aug. 2, 2019, provisional application No. 62/741,642, filed on Oct. 5, 2018.

(51) Int. Cl.
*H01R 13/52* (2006.01)
*A61N 1/375* (2006.01)
(Continued)

(52) U.S. Cl.
CPC ....... *H01R 13/5219* (2013.01); *A61N 1/3754* (2013.01); *H01R 13/2407* (2013.01);
(Continued)

(58) Field of Classification Search
CPC ............ H01R 13/5219; H01R 13/2407; H01R 13/621; H01R 43/205; H01R 2201/12;
(Continued)

(56) References Cited

U.S. PATENT DOCUMENTS 4,516,820 A 5/1985 Kuzma
7,534,127 B2 5/2009 Parker et al.
(Continued)

OTHER PUBLICATIONS

International Searching Authority, International Search Report and Written Opinion for International Application No. PCT/US2019/054765, dated Dec. 11, 2019, (19 pages), United States Patent and Trademark Office, USA.

*Primary Examiner* — Gary F Paumen
(74) *Attorney, Agent, or Firm* — ALSTON & BIRD LLP

(57) ABSTRACT

Embodiments are provided that enable an implantable connector, along with related apparatuses, devices, systems, methods, computing devices, computing entities, and/or the like to serve patients with neural interfaces requiring connectors with higher channel densities (>0.05 ch/mm$^3$) or higher channel counts (>32) than is practical with conventional implant-connector technology.

19 Claims, 26 Drawing Sheets

(51) Int. Cl.
*H01R 13/24* (2006.01)
*H01R 13/621* (2006.01)
*H01R 43/20* (2006.01)
*H05K 5/00* (2006.01)
*H05K 5/02* (2006.01)
*H05K 5/04* (2006.01)

(52) U.S. Cl.
CPC ......... *H01R 13/621* (2013.01); *H01R 43/205* (2013.01); *H05K 5/0008* (2013.01); *H05K 5/0095* (2013.01); *H05K 5/0247* (2013.01); *H05K 5/04* (2013.01); *H01R 2201/12* (2013.01)

(58) Field of Classification Search
CPC .. A61N 1/3754; H05K 5/0008; H05K 5/0095; H05K 5/0247; H05K 5/04
See application file for complete search history.

(56) References Cited

U.S. PATENT DOCUMENTS

| 10,149,980 B2* | 12/2018 | Shah | ................ H01R 13/2421 |
| 10,608,354 B2* | 3/2020 | Shah | .................... H05K 5/006 |
| 2016/0380381 A1 | 12/2016 | Shah et al. | |
| 2018/0277970 A1 | 9/2018 | Shah | |

\* cited by examiner

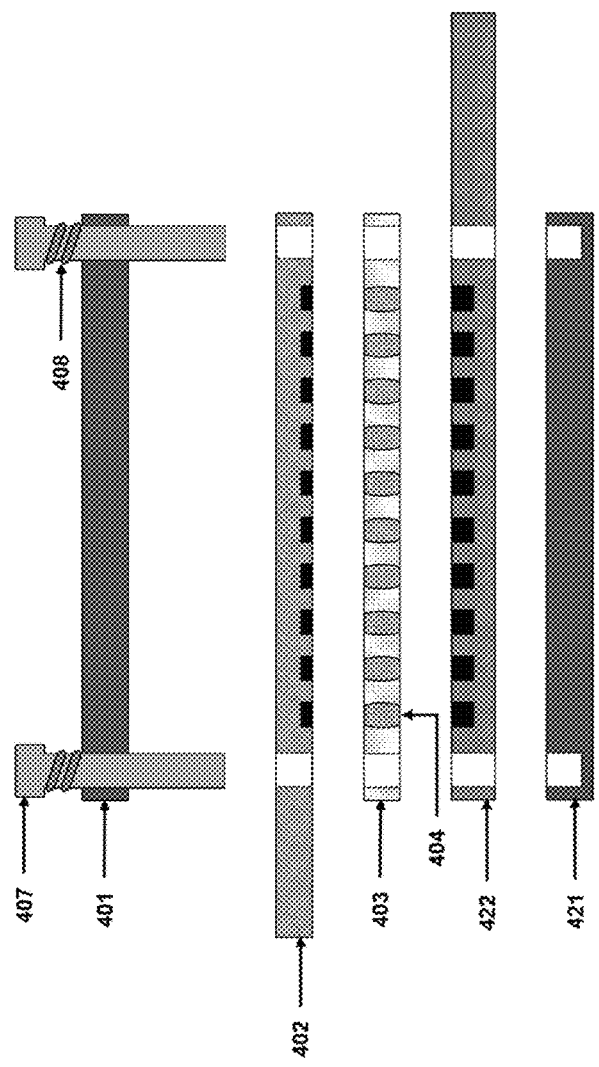
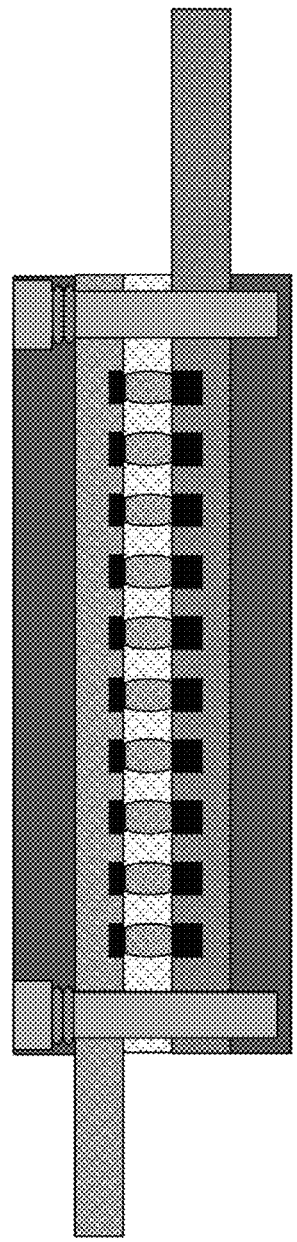
FIG. 7A
FIG. 7B

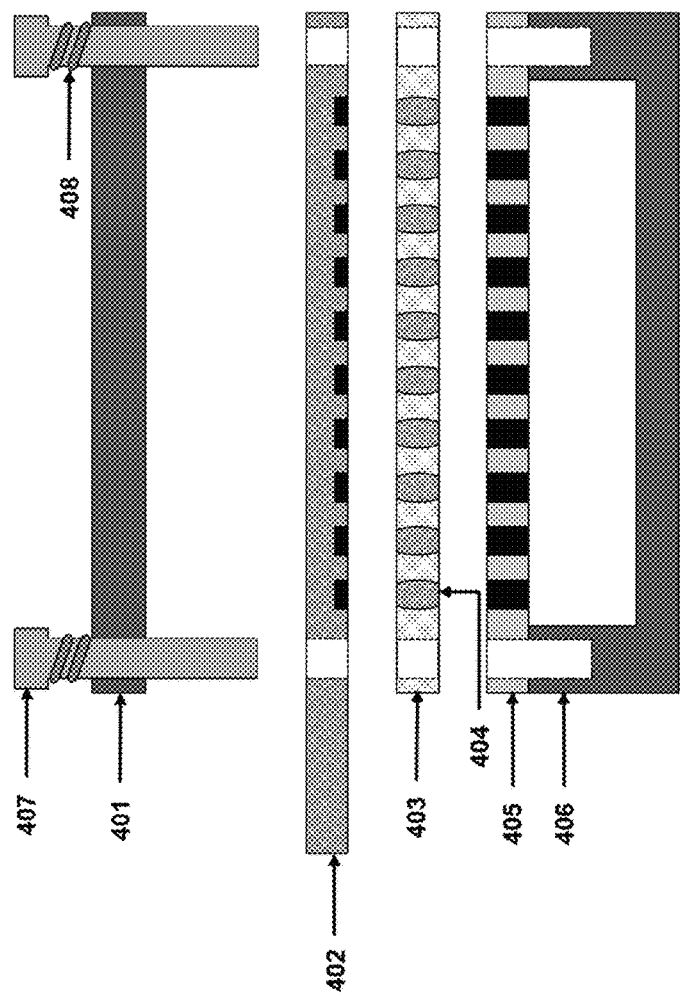
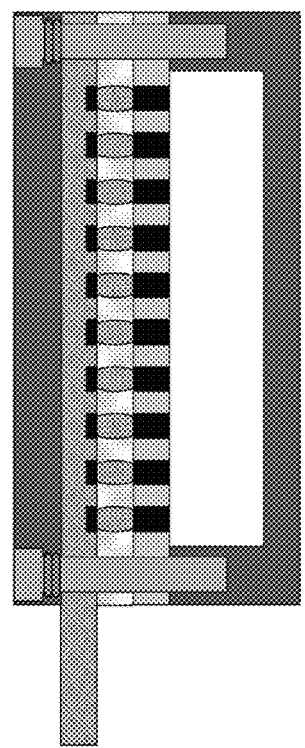

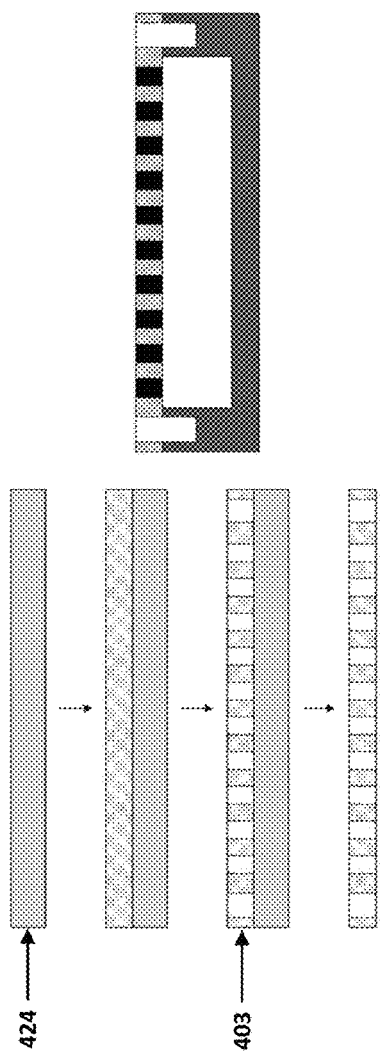
FIG. 11A
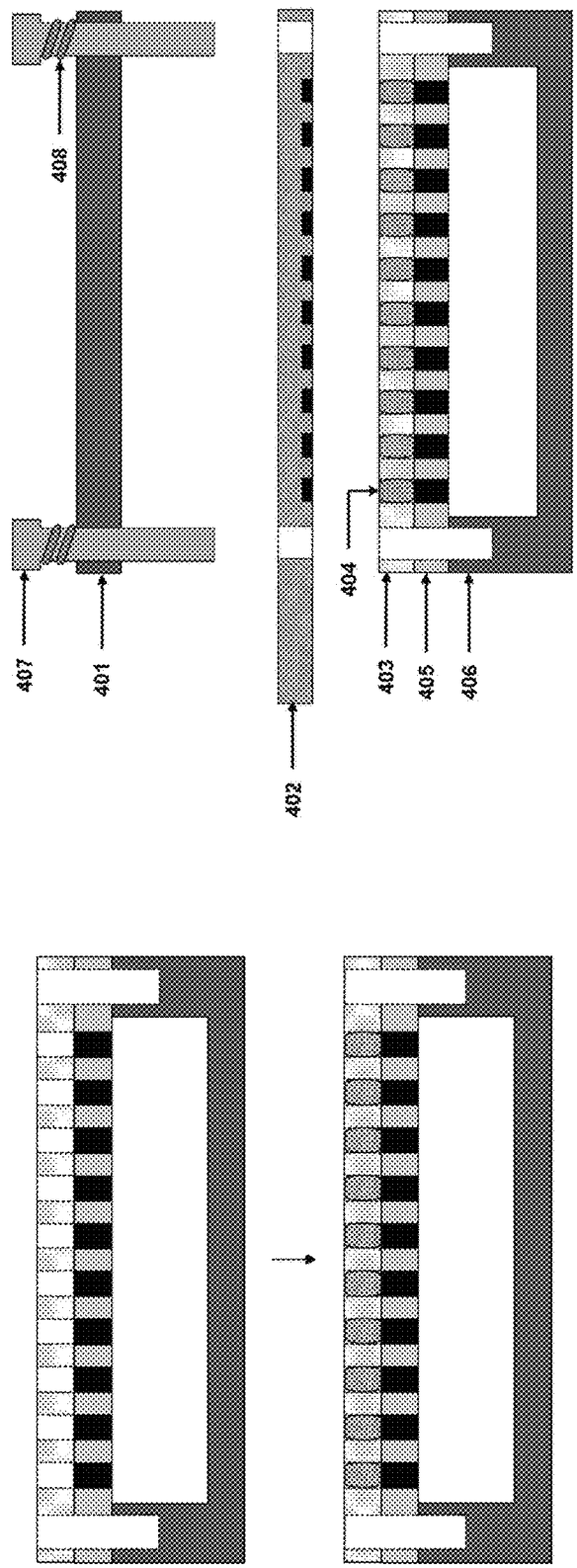
FIG. 11C
FIG. 11B

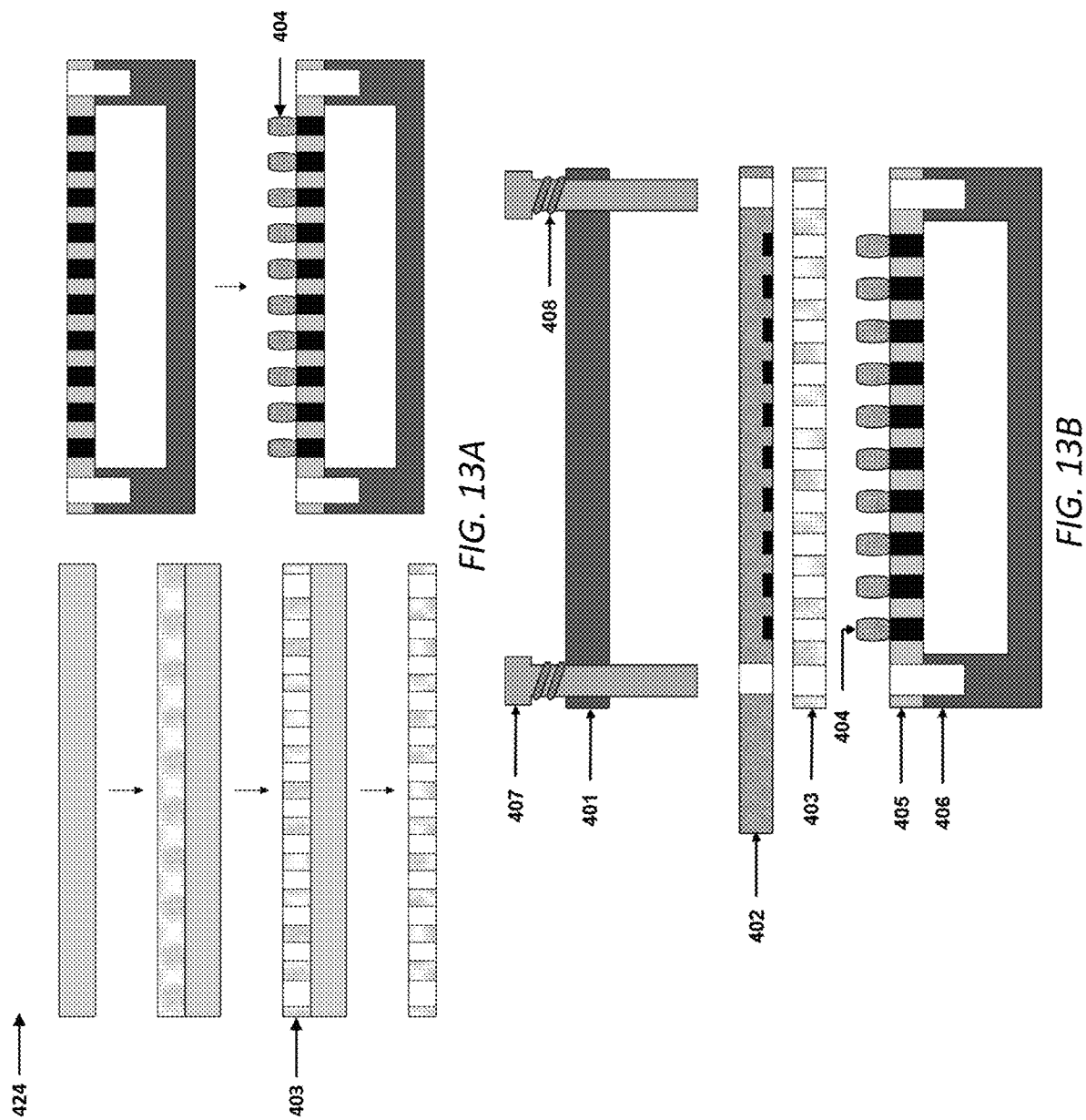

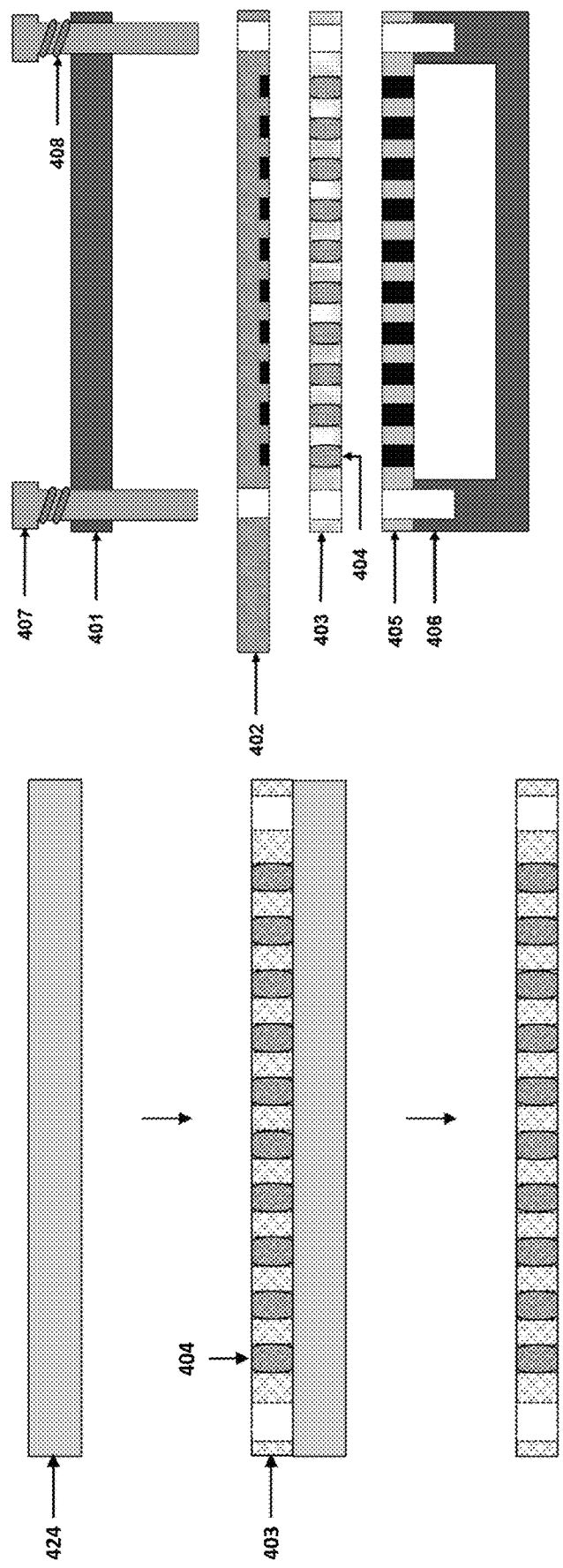

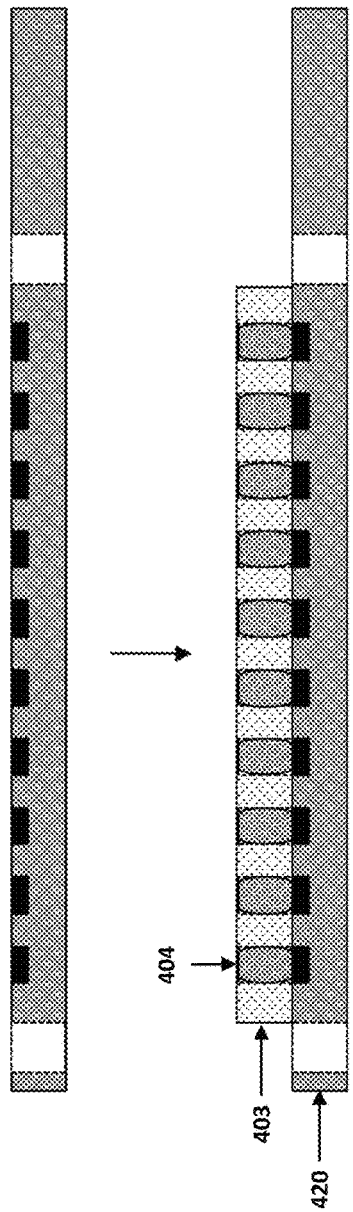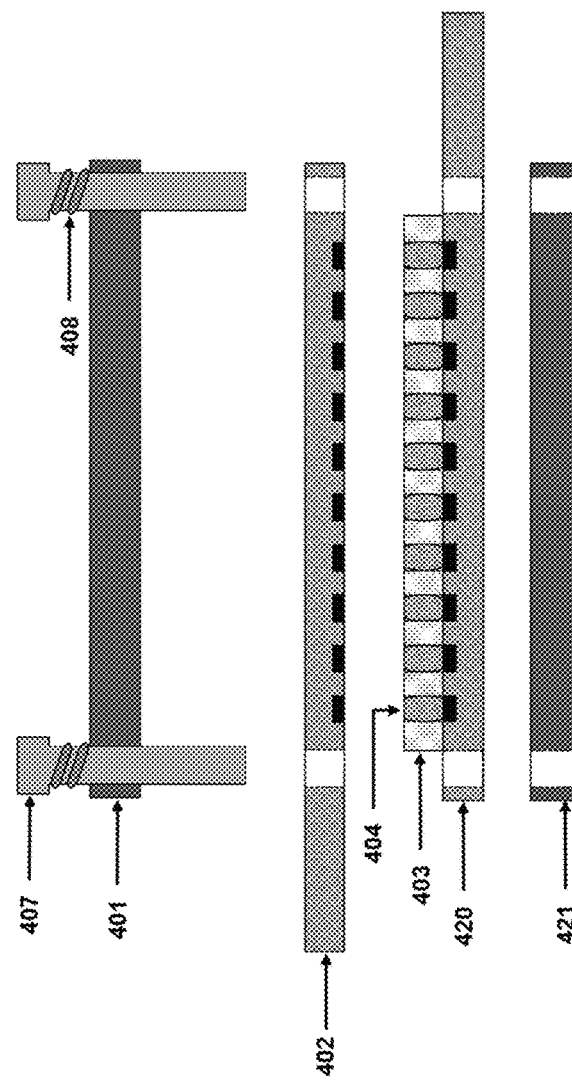

RELIABLE MINIATURE IMPLANTABLE CONNECTOR WITH HIGH CHANNEL DENSITY AND METHODS OF USING THE SAME

CROSS-REFERENCE TO RELATED APPLICATIONS

The present application is a U.S. National Stage entry of International Application No. PCT/US2019/054765, titled "RELIABLE MINIATURE IMPLANTABLE CONNECTOR WITH HIGH CHANNEL DENSITY AND METHODS OF USING THE SAME," filed Oct. 4, 2019, which international application claims priority to U.S. Provisional Application Ser. No. 62/882,302, titled "RELIABLE MINIATURE IMPLANTABLE CONNECTOR WITH HIGH CHANNEL DENSITY AND METHODS OF USING THE SAME," filed Aug. 2, 2019, and to U.S. Provisional Application Ser. No. 62/741,642, titled "RELIABLY MINIATURE IMPLANTABLE CONNECTOR WITH HIGH CHANNEL DENSITY AND METHODS OF USING THE SAME," filed Oct. 5, 2018, the contents of all of which are incorporated herein by reference in their entirety.

STATEMENT REGARDING GOVERNMENT SPONSORED RESEARCH OR DEVELOPMENT

The invention was made with government support under R21 EB028079 awarded by the National Institutes of Health (NIH). The government has certain rights in the invention.

BACKGROUND

As neural-interface technology has advanced to higher channel counts and higher channel densities to improve stimulation targeting and to minimize side effects, the benefits derived by patients have also typically increased. Leading examples include the progress seen in cochlear implants, deep-brain stimulation (DBS), retinal prosthetics, and brain-machine interfaces (BMI). Although cochlear implants started out as single-channel devices that invoke a sensation of sound, higher-channel-count cochlear implants are needed to enable speech discrimination. Similarly, the functional sight restored to patients with retinal prosthetics is significantly increased as the number of independent channels of visual information increases. The advance of DBS technologies to higher channel counts and densities is being driven by the increasing need to steer current for more targeted stimulation of smaller anatomical regions and to minimize side effects. Finally, BMI are driving the development of the highest-channel-count neural implants for both recording independent motor-control information and stimulating independent sensory-feedback information at greater scale and higher resolution.

Although potentially significant benefits for patients have successfully driven the development of higher-channel-count neural interfaces, the lack of advancement in implant-packaging technology continues to impose barriers that significantly impede their successful translation to the clinic. An analysis of implant-packaging-technology development reveals that despite advances in implant electronics, batteries, enclosures, and even high-feedthrough-density/count headers, the lack of advancement in implant connector technology has been the limiting factor. Specifically, implant applications requiring the ability to disconnect/reconnect an interface lead from/to an implant package are limited by existing implantable connector technology to low channel counts (8 ch/lead). In contrast, implant applications that require high channel counts (>32) are currently permanently bonded to high-feedthrough-count headers. As a consequence, changes to such implants require the entire system, including the interface itself, to be fully explanted and re-implanted, which typically causes significant tissue damage. The unavailability of high-channel-count (>32) and high-channel-density connectors currently impedes the ability to demonstrate and ultimately translate neuro-technologies that need re-connectability and high channel counts (>32).

Bearing in mind the above-detailed particulars, exemplary methods used to connect neural interfaces with implanted packaged electronics can be organized into two groups. The first connection-method group uses permanent bonding to achieve irreversible electrical connections. Non-limiting examples of such connection methods include soldering, conductive adhesives, and thermal-compression bonding. Irreversible bonding methods are used out of necessity when the channel counts are high and/or the volume available for such connections is highly limited. Leading clinical applications that use irreversible bonding between interfaces and packaged electronics include cochlear implants, retinal prosthetics, and BMIs. To replace or upgrade any of these devices, the entire system, including the interface, must be explanted and then re-implanted. Doing so will cause damage to the target neural tissue (e.g., re-tacking to the retina, re-implanting probe arrays into the cortex, etc.).

The second connection-method group uses an engineered connector that allows the interface lead to be disconnected and then re-connected. Nearly all commercial neural implants with connectors use technology configured as follows: (1) with toroidal springs to provide multiple points of contact, reliably low-impedance contacts, and consistent contact force over time, (2) with good channel-to-channel isolation achieved with silicone bushings, (3) with low and consistent insertion force, (4) with ease of use for surgeons, and (5) with high connector mating cycle lifetime. However, a limitation of this connector technology is that its low volumetric channel density (<0.05 ch/mm$^3$) results in bulky devices as the channel counts are linearly scaled up to higher channel counts (e.g., 32-channel SCS system developed by Boston Scientific).

Through applied effort, ingenuity, and innovation, many deficiencies of such systems have been solved by developing solutions that are in accordance with the embodiments of the present invention, many examples of which are described in detail herein. Successful development of an advanced implantable connector technology, as is disclosed herein, will propel the clinical demonstration of miniature high-channel-count neural interfaces that are best left integrated into tissue during any changes to the implanted electronics (e.g., battery changes, upgraded electronics, etc.). Applications include: invasive high-channel-count (≥100 channels) brain interfaces (e.g., BMI, DBS) and invasive high-channel-count ≥100 channels) nerve interfaces (e.g., prosthesis control and sensory feedback).

BRIEF SUMMARY

To meet the above-described needs and others, exemplary embodiments of the present invention provide an implantable connector, along with related apparatuses, devices, systems, methods, computing devices, computing entities, and/or the like to serve patients with neural interfaces requiring connectors with higher channel densities (>0.05 ch/mm$^3$) or higher channel counts (>32) than is practical with conventional implant-connector technology; especially when the ability to disconnect the interface from implanted electronics is needed to perform battery changes, replacement, or upgrades without disturbing interfaces that have become integrated into delicate and sensitive neural tissue. Clinical applications for the exemplary embodiments described include high-channel-count brain-machine-interfaces (BMI) to restore sensory and motor function, high-channel-count nerve interfaces for sensing and controlling state-of-the-art prosthetics limbs, miniature high-channel-density devices to interface with nerves for bioelectronic-medicine applications, and even next-generation deep-brain stimulation (DBS) systems.

Various embodiments will thus, as non-limiting examples, improve implantable connector technology in at least three independent ways: by developing a reliable miniaturized implant-gasket technology so that higher channel densities are possible in implantable connectors without compromising channel-to-channel isolation; by developing miniaturized mechanisms for multi-point force-maintained low-impedance electrical contact between high-channel-density interface leads and high-feedthrough-density implant headers; and by developing a reliable clamping mechanism that can deliver and maintain enough constant force to achieve reliable channel-to-channel isolation and low contact impedance throughout the lifetime of the neural interface.

Various embodiments provide, as a non-limiting example, an implantable connector providing a high-channel density interconnect between high-pad-array-density interface leads and high-feedthrough-density implant headers. The implantable connector is configured for disconnecting and reconnecting with a neural interface, as needed, to change and/or upgrade electronics, batteries, or the like. Machining and micromachining are used to achieve accurate and uniform features for high channel density.

BRIEF DESCRIPTION OF THE DRAWINGS

Figure 1A:
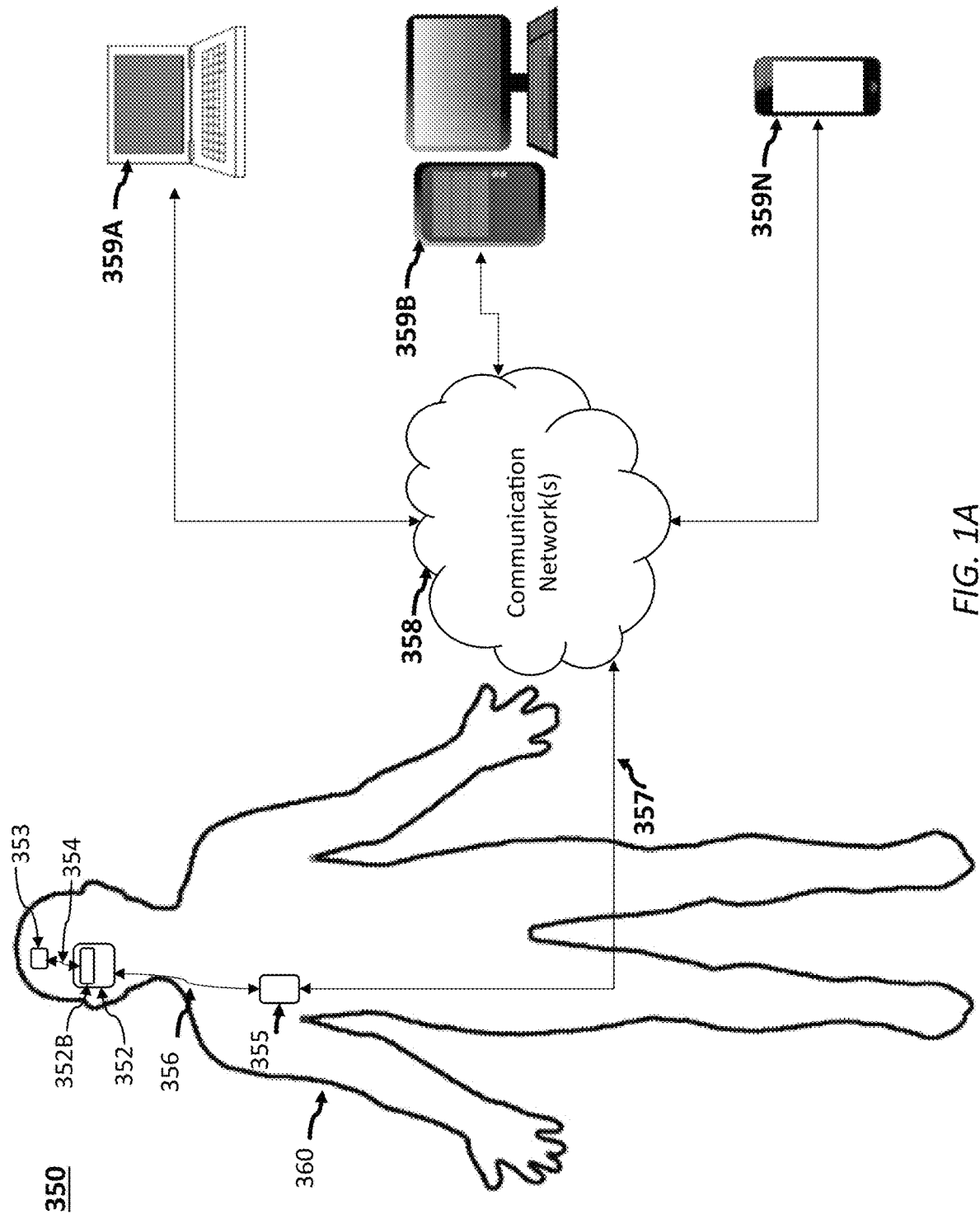
Figure 1B:
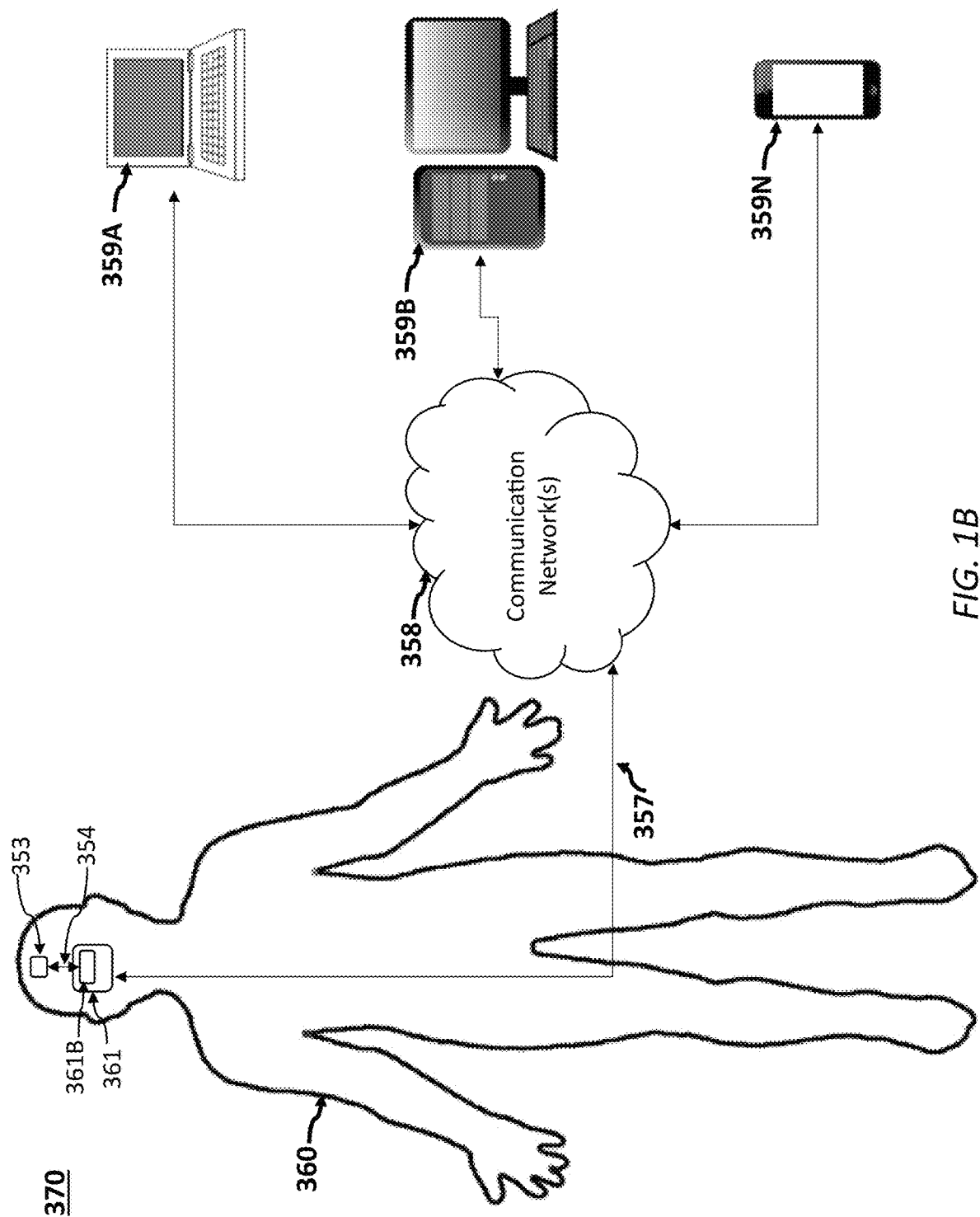
Figure 1C:
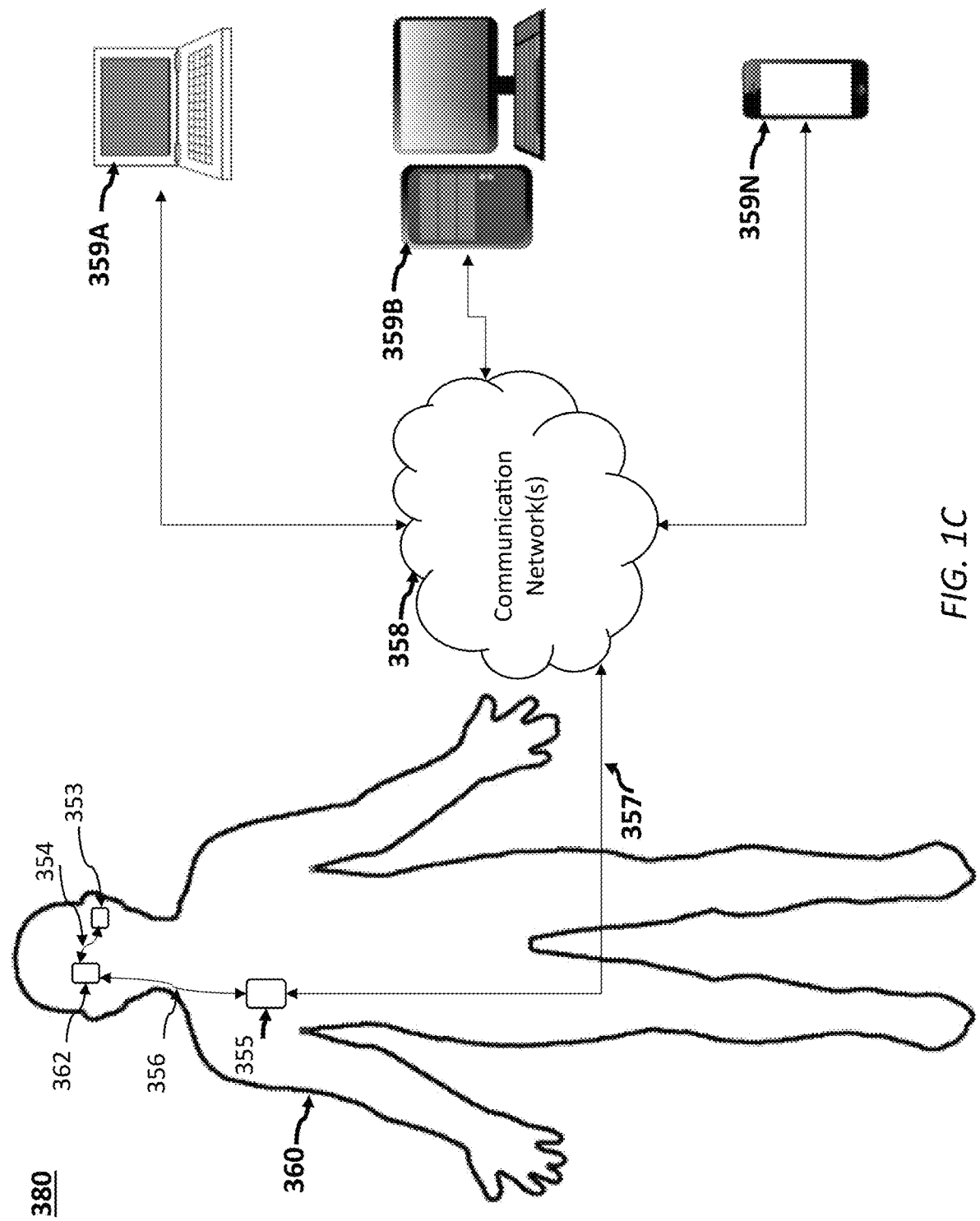
Figure 2A:
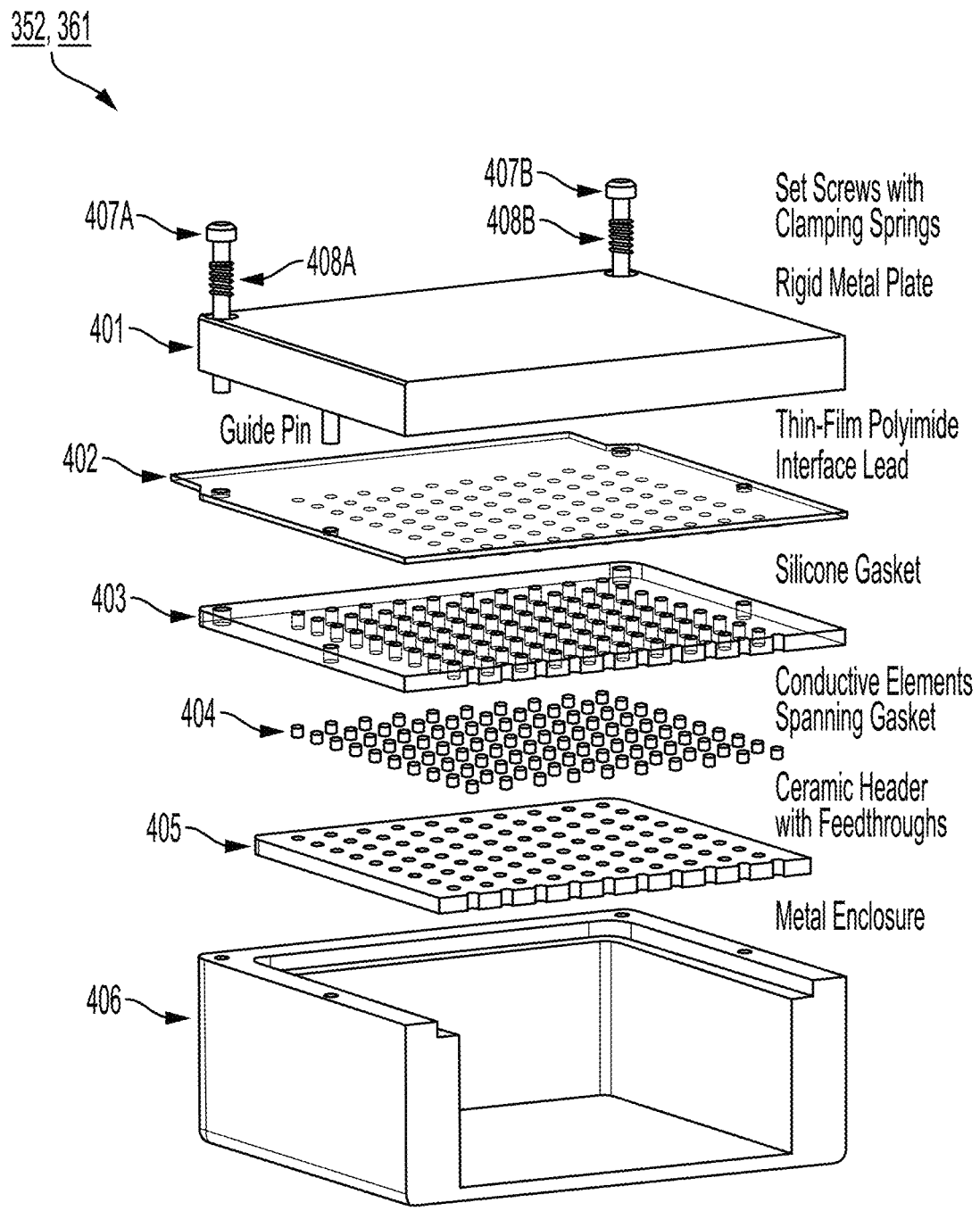
Figure 2B:
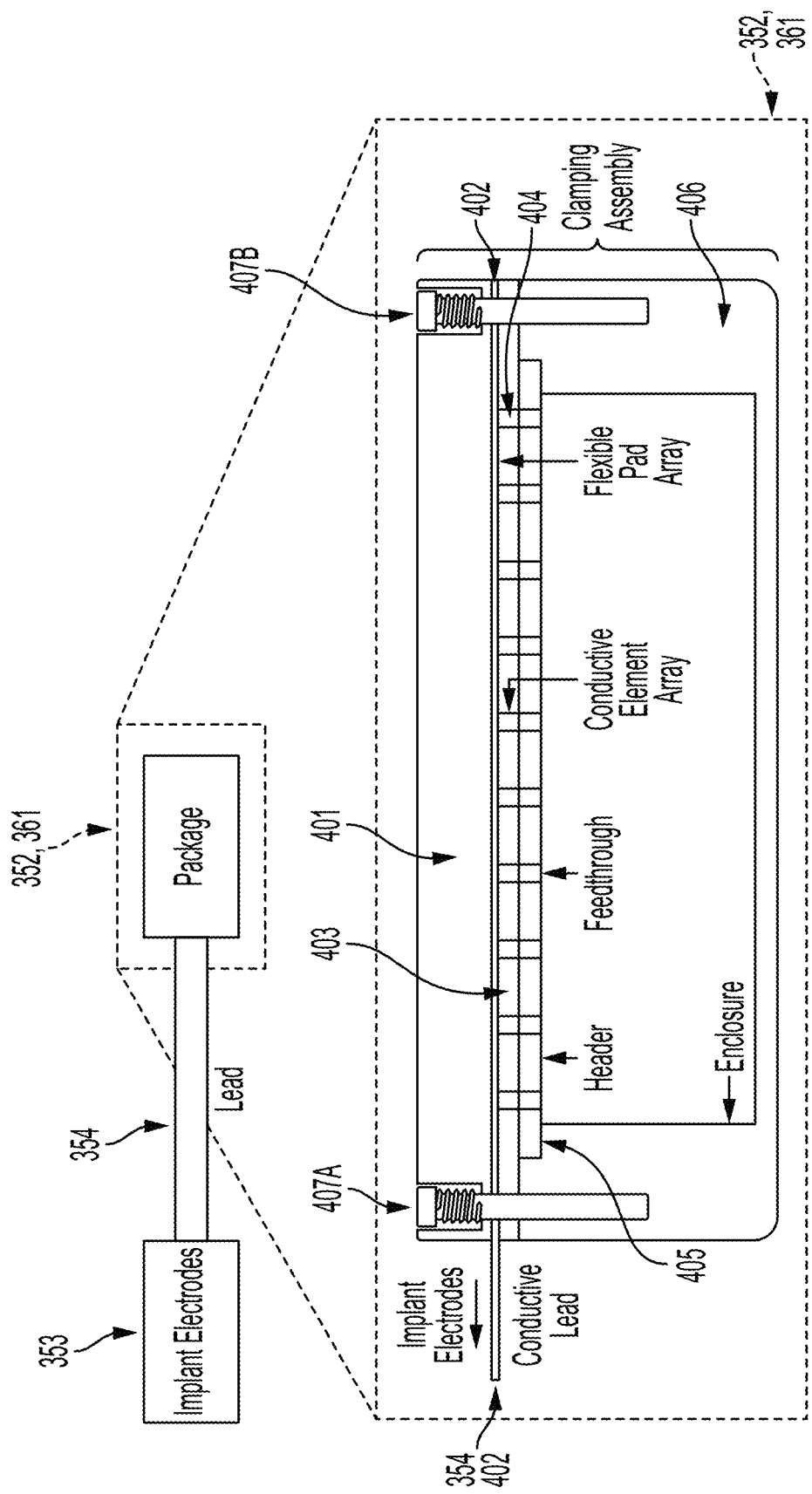
Figure 3A:
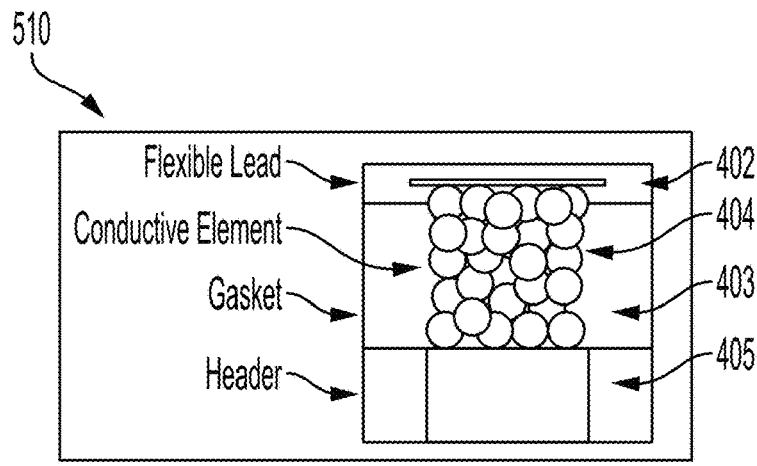
Figure 3B:
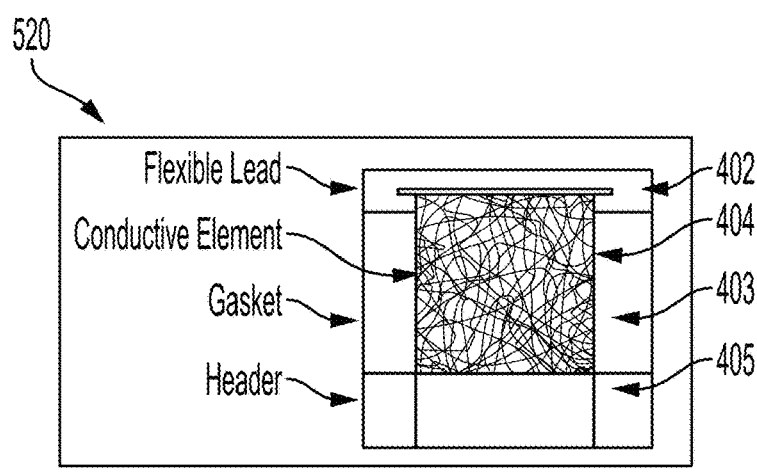
Figure 3C:
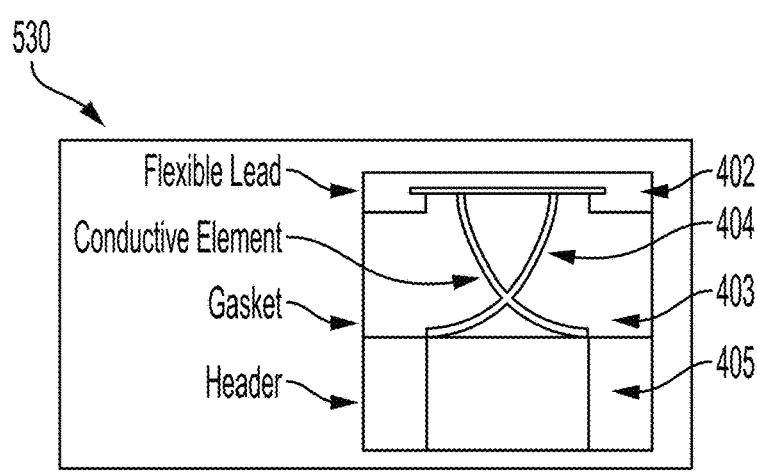
Figure 4:
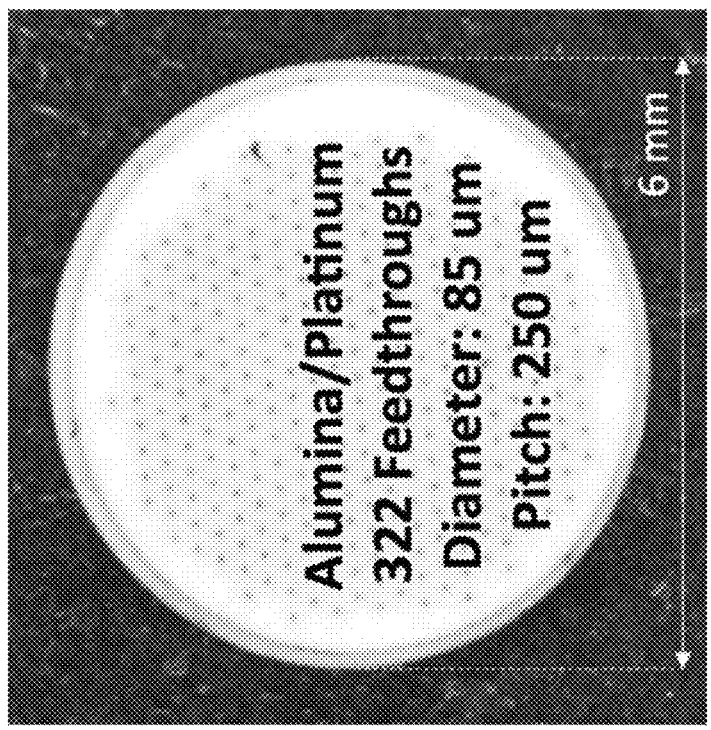
Figure 5:
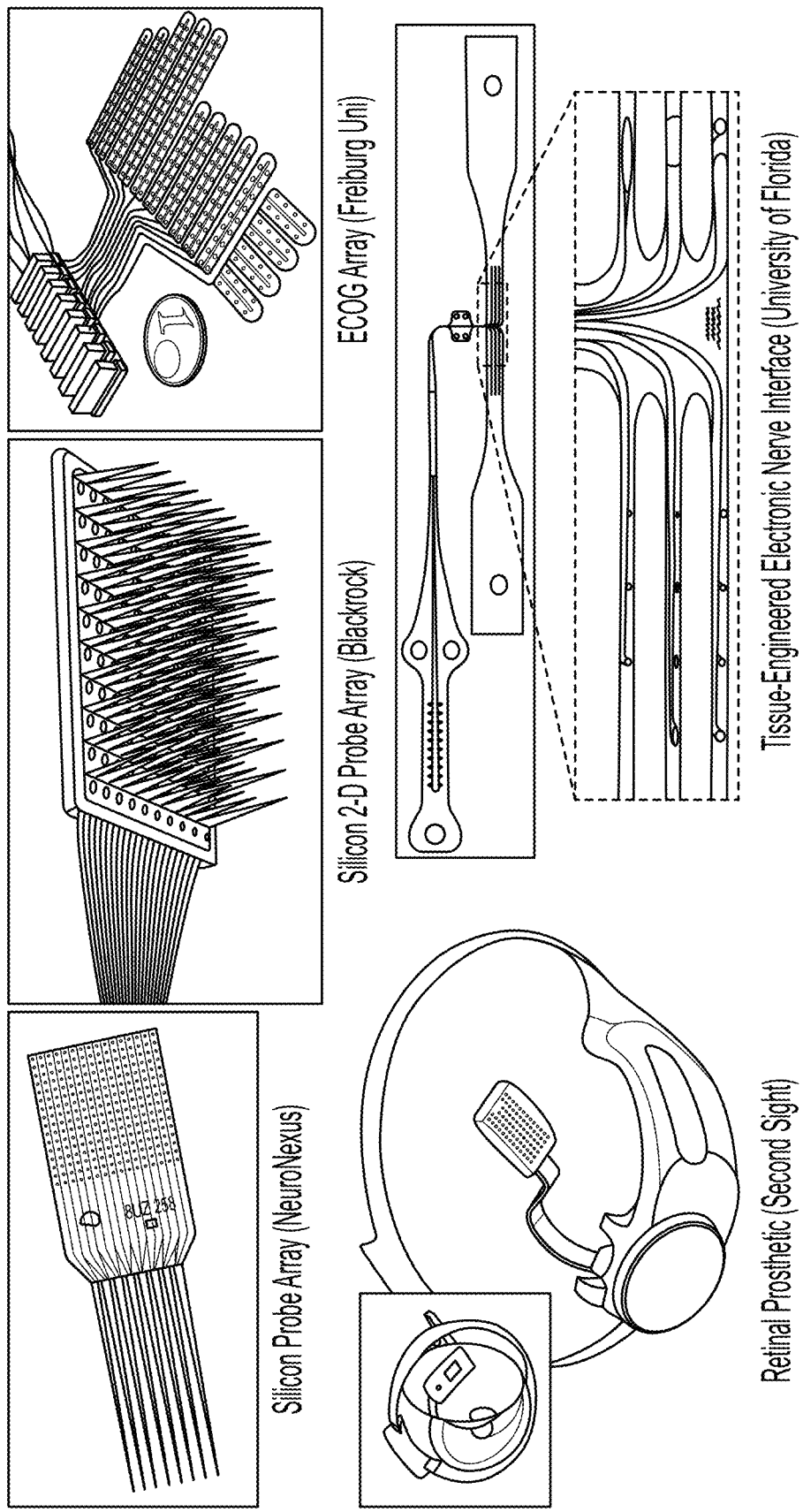
Figure 6A:
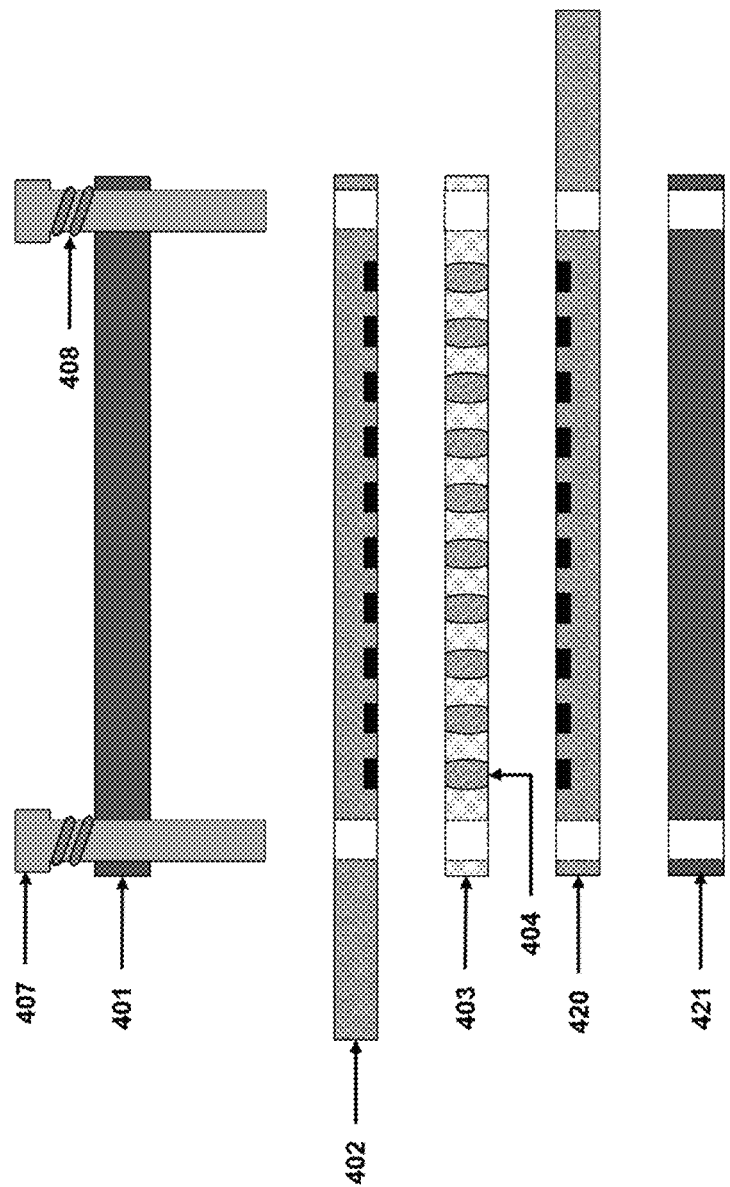
Figure 6B:
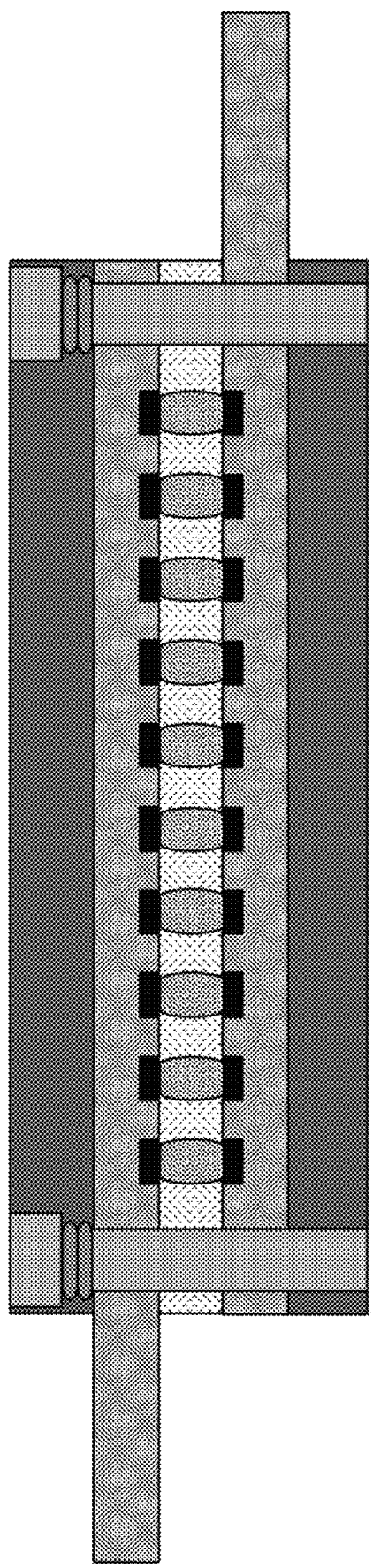
Figure 9A:
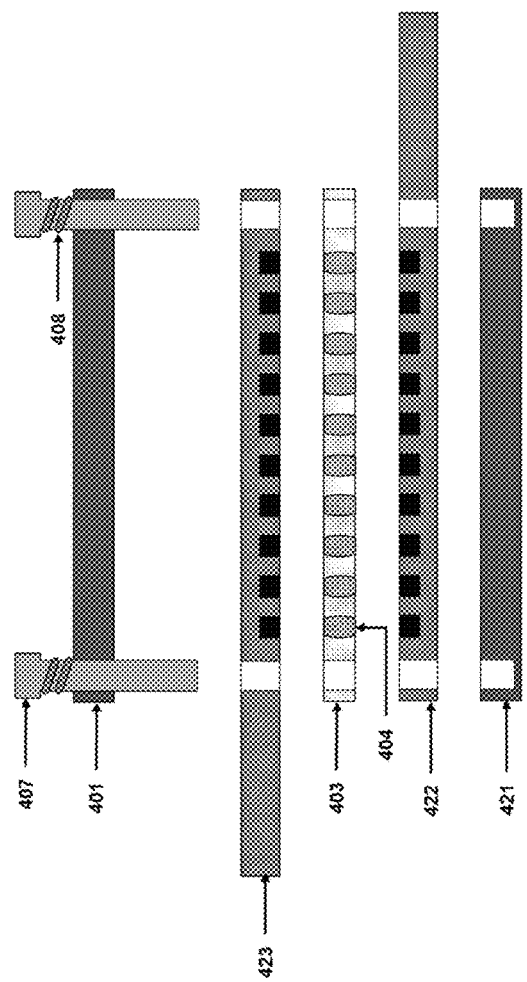
Figure 9B:
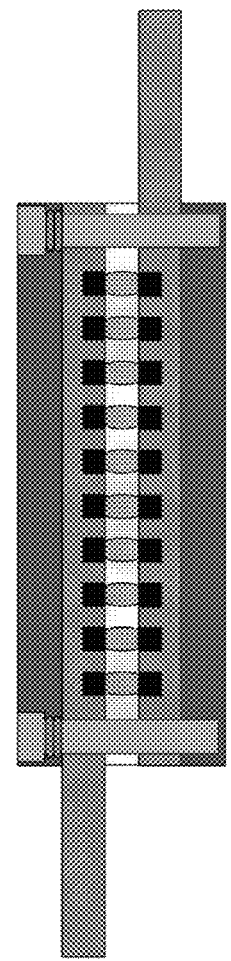
Figure 10A:
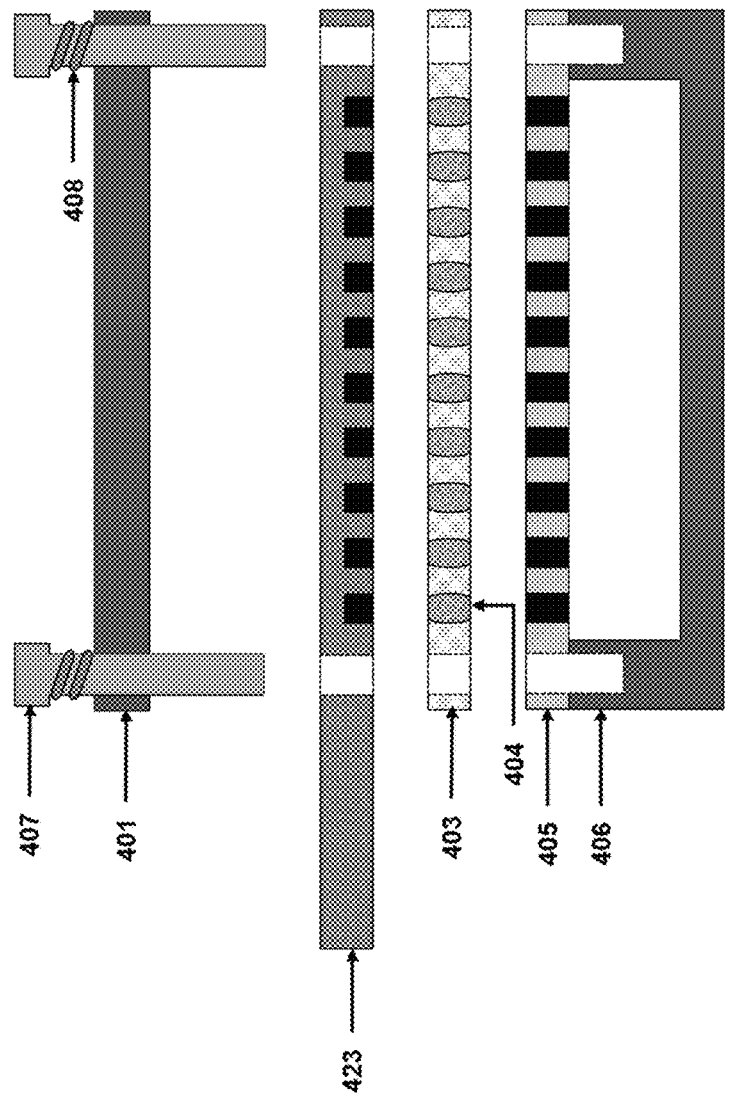
Figure 10B:
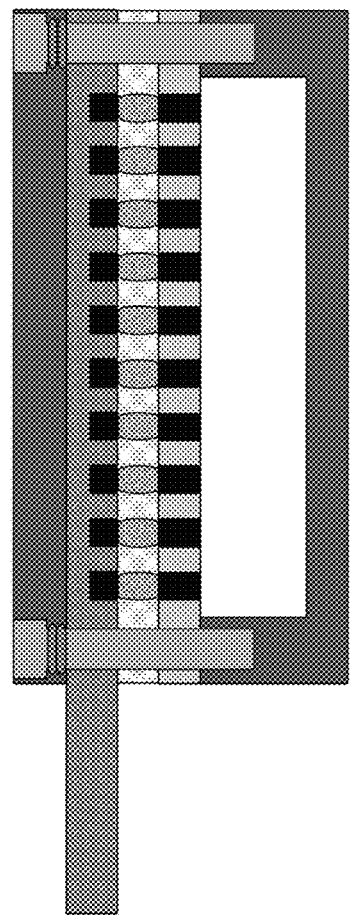
Figure 12B:
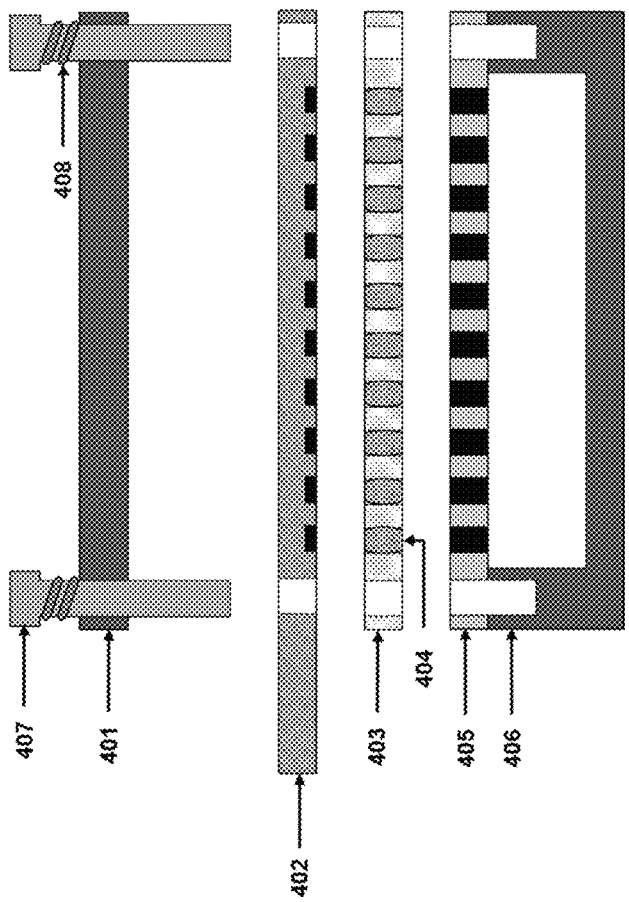
Figure 12A:
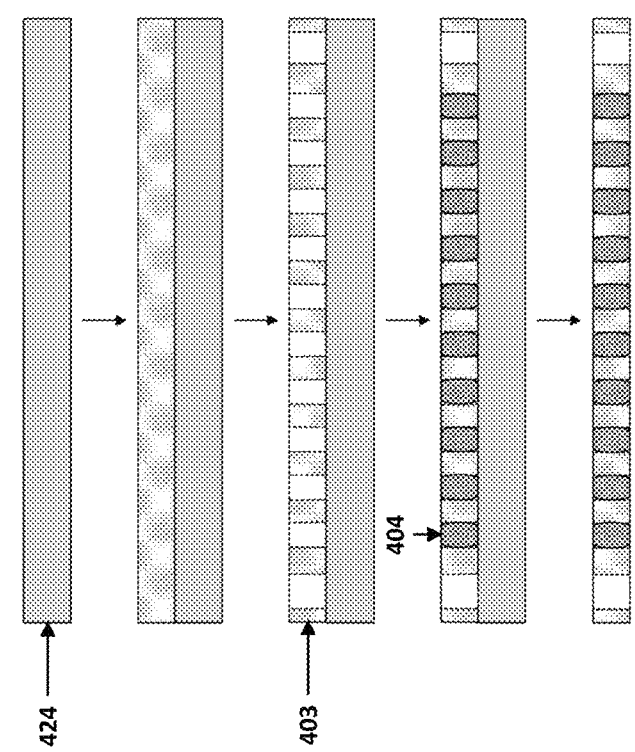
Figures 14A, 14B:
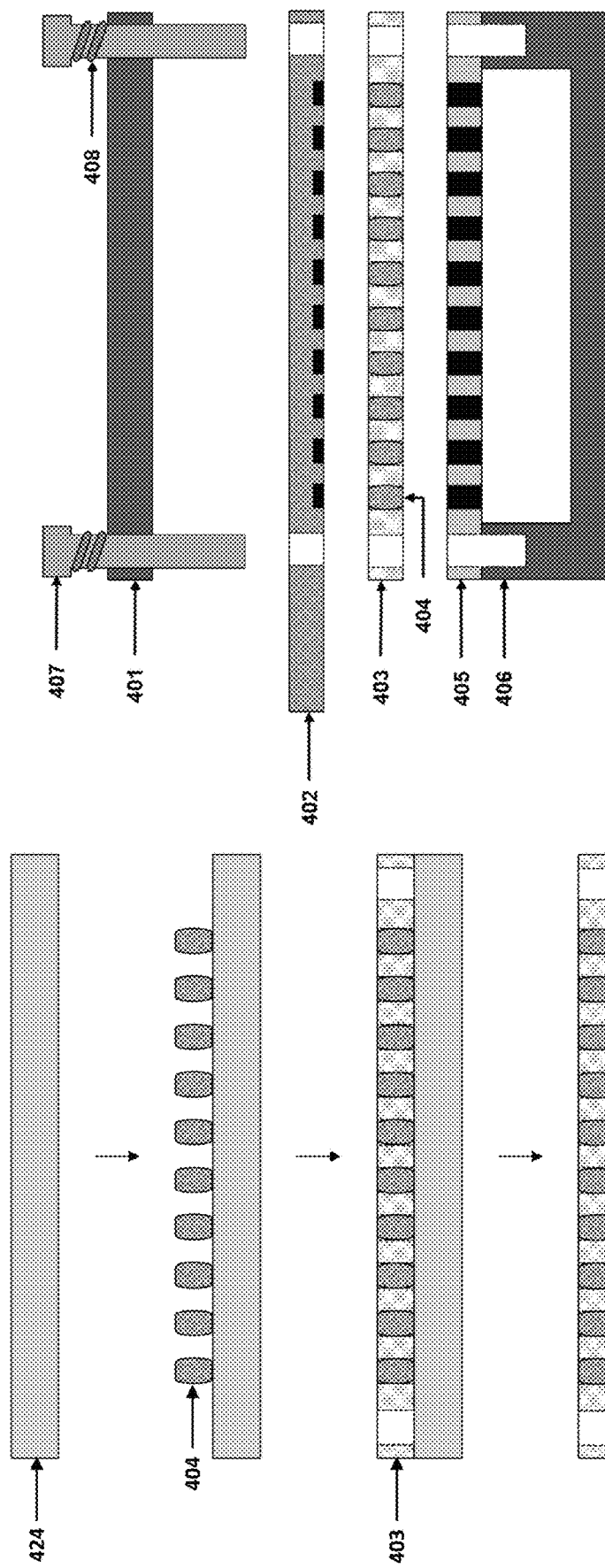
Figure 16A:
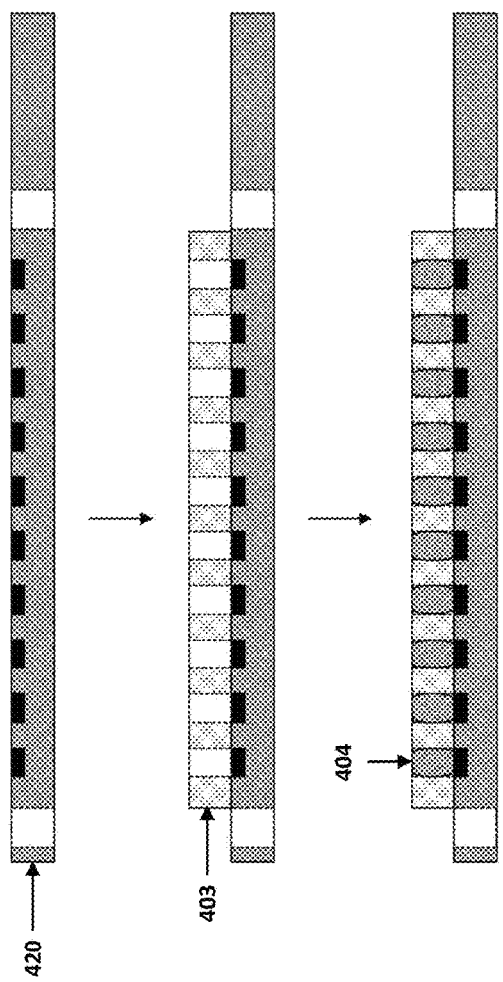
Figure 16B:
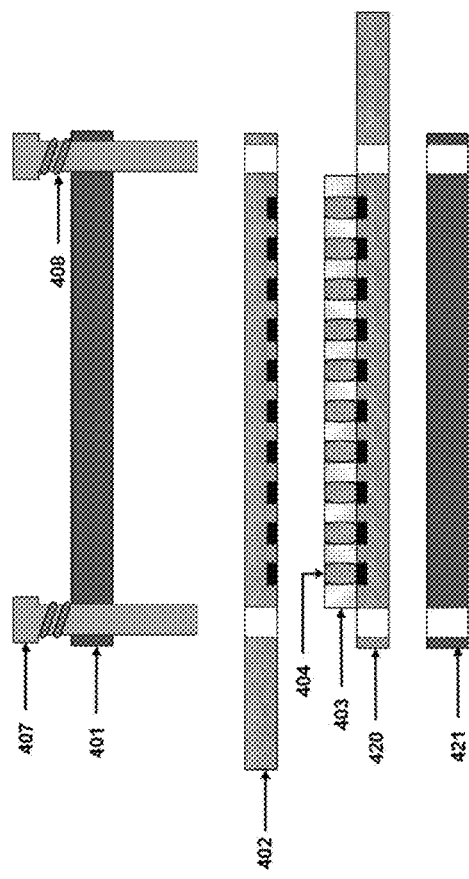
Figure 17A:
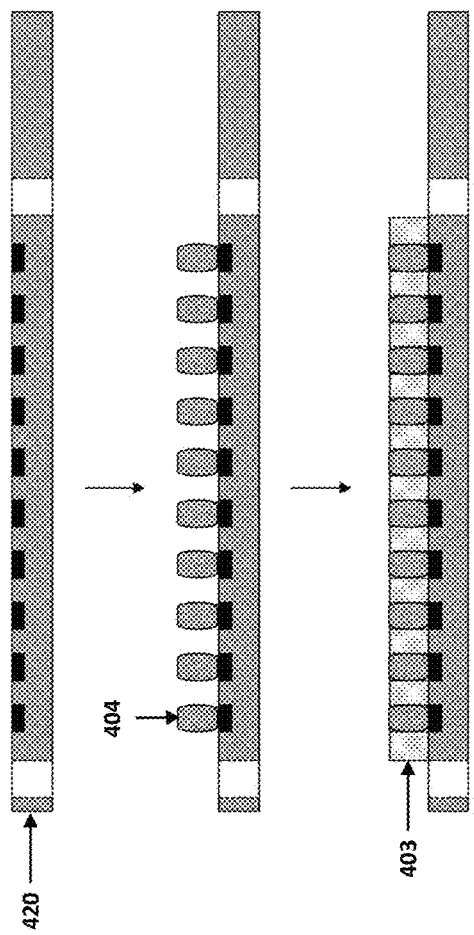
Figure 17B:
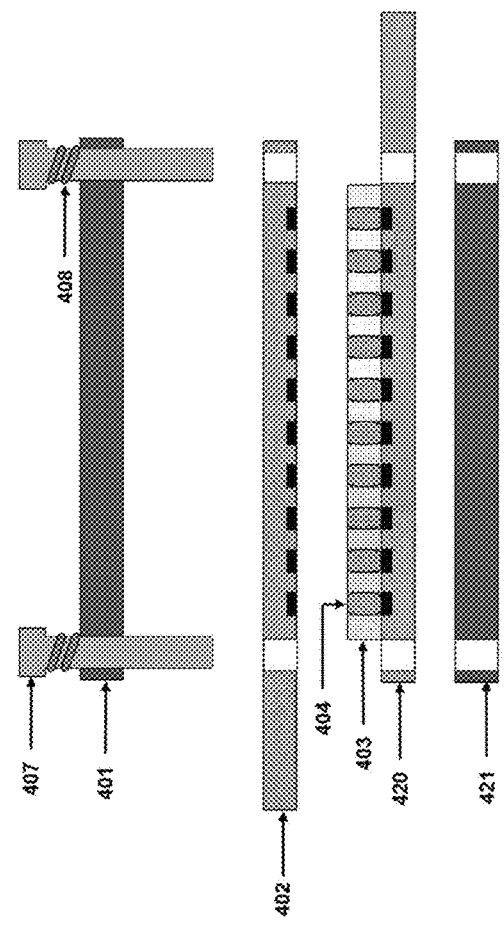
Figure 19A:
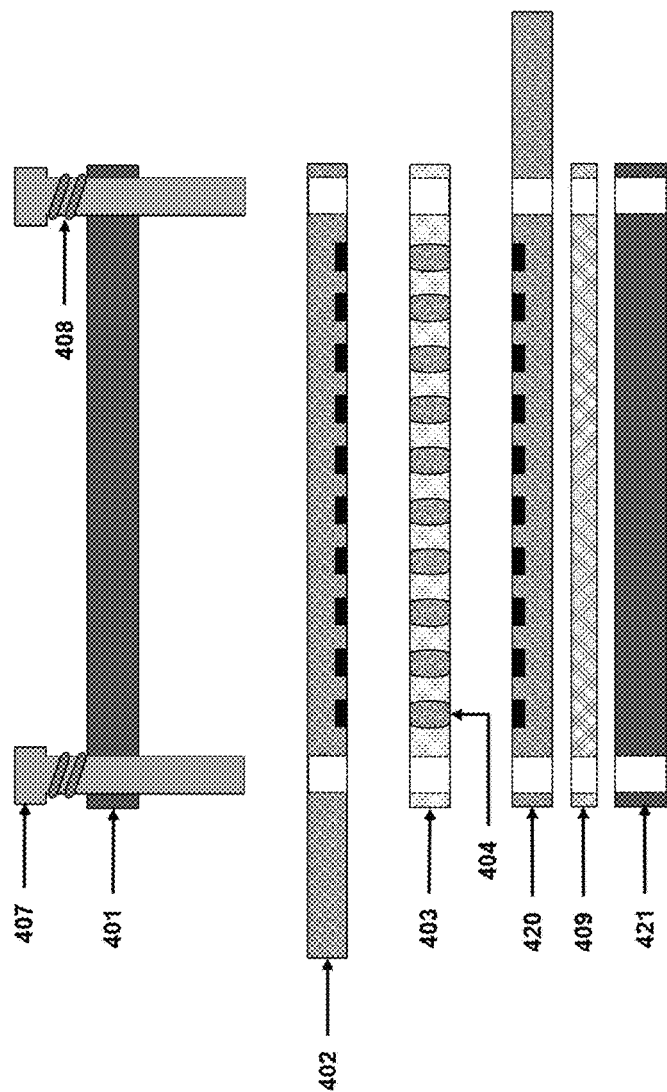
Figure 19B:
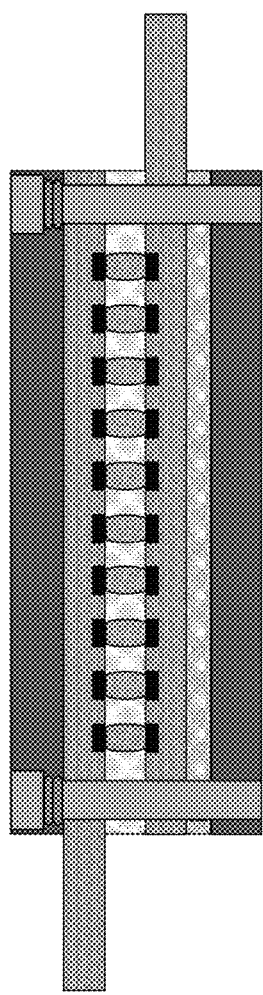
Figure 20:
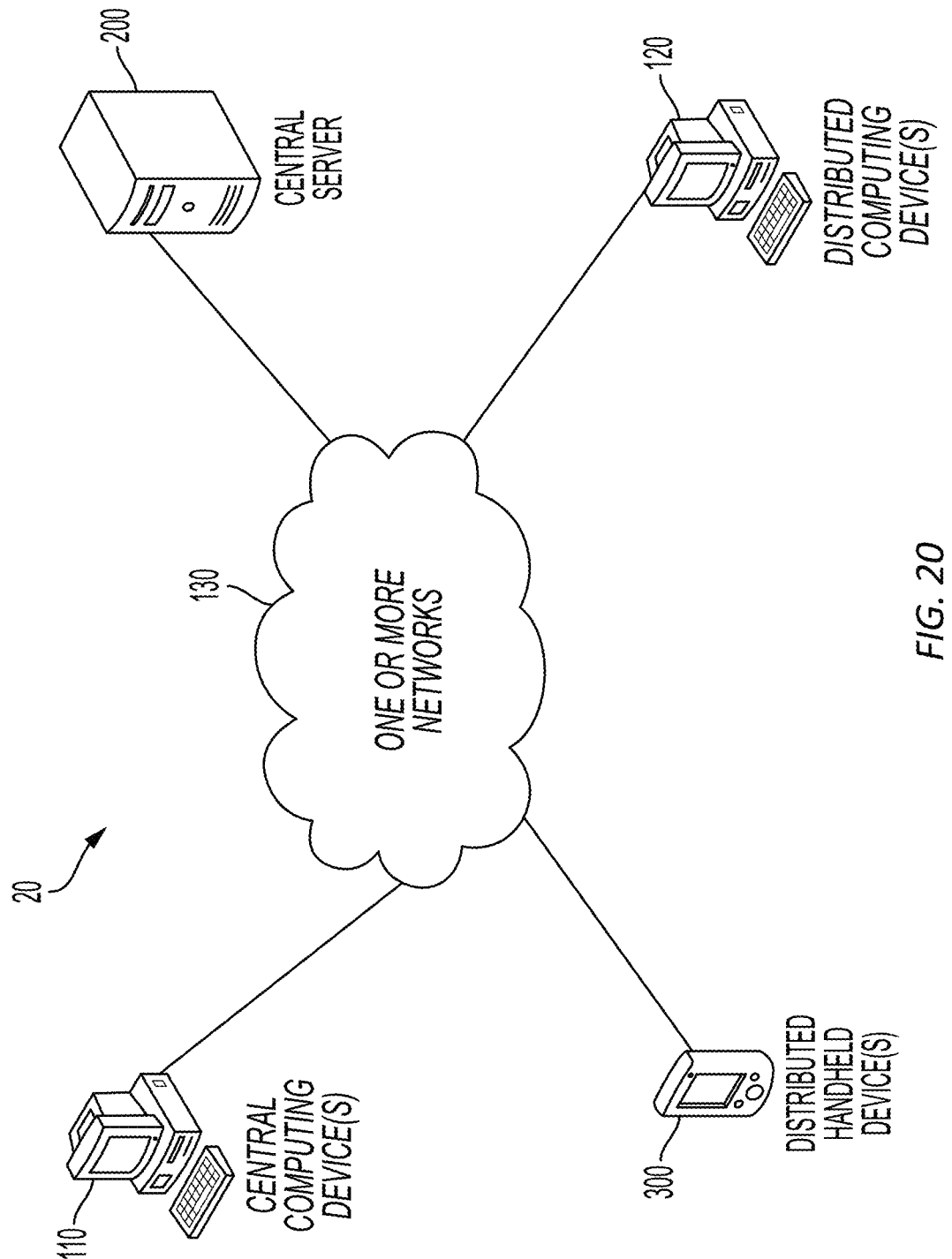
Figure 21A:
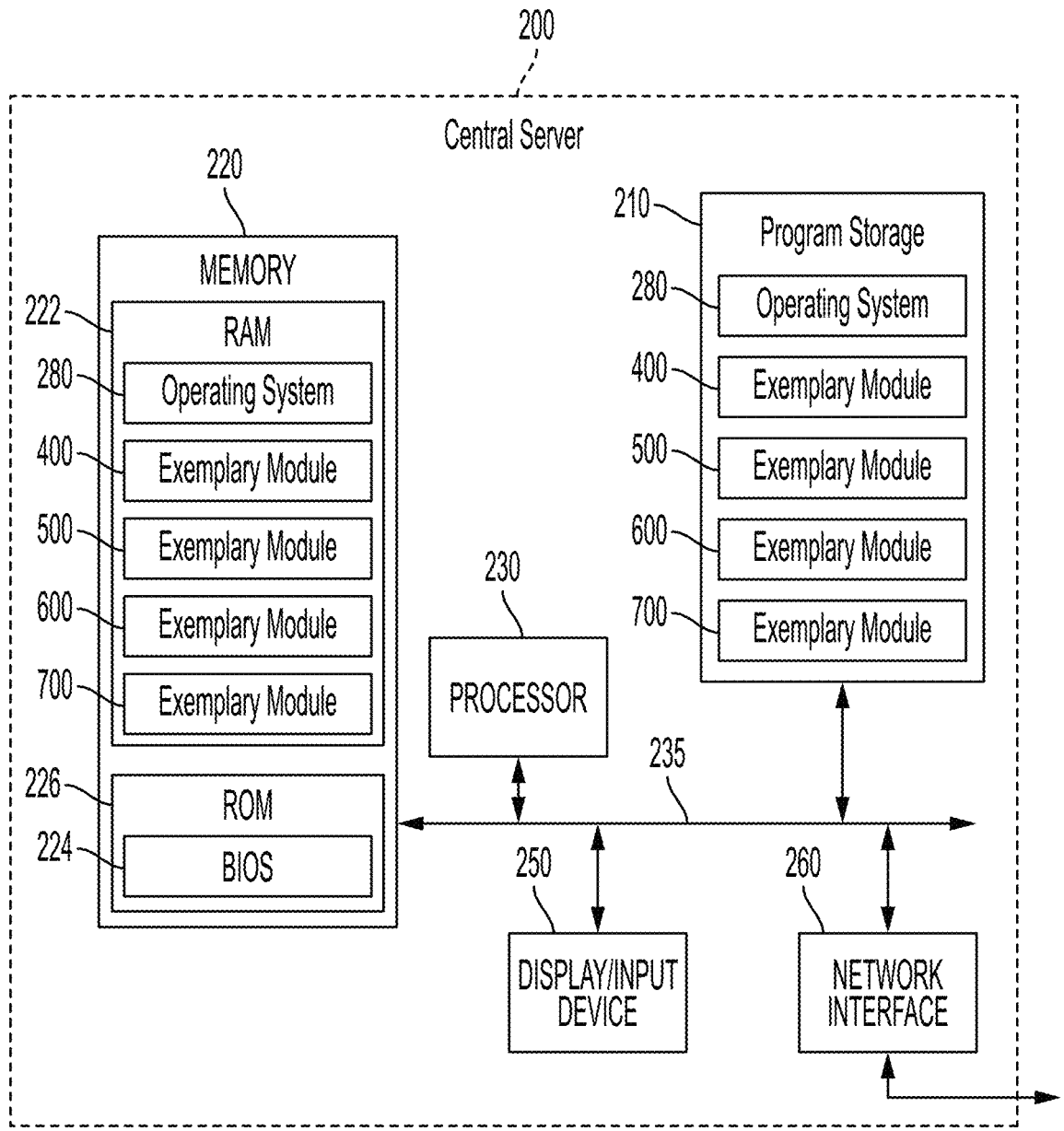
Figure 21B:
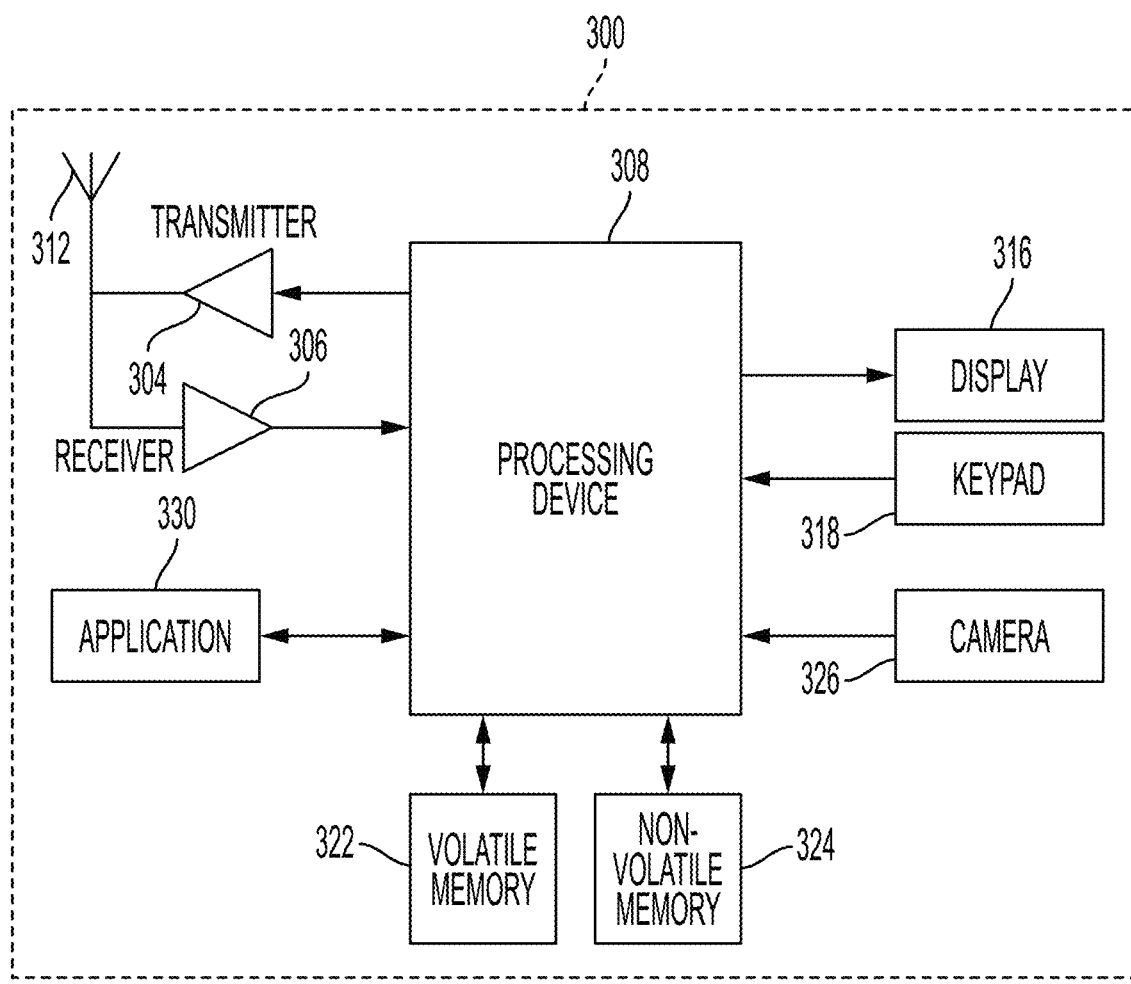

Having thus described the invention in general terms, reference will now be made to the accompanying drawings, which are not necessarily drawn to scale, and wherein:

FIG. 1A illustrates an exemplary neural implant system according to various exemplary embodiments of the present disclosure;

FIG. 1B illustrates an exemplary neural implant system according to various exemplary embodiments of the present disclosure;

FIG. 1C illustrates an exemplary neural implant system according to various exemplary embodiments of the present disclosure;

FIG. 2A illustrates an exploded view of an exemplary implant apparatus according to various exemplary embodiments of the present disclosure;

FIG. 2B illustrates a compressed view of an exemplary implant apparatus according to various exemplary embodiments of the present disclosure;

FIG. 3A illustrates an exemplary conductive-element configuration 510 for use with various exemplary embodiments of the present disclosure;

FIG. 3B illustrates an exemplary conductive-element configuration 520 for use with various exemplary embodiments of the present disclosure;

FIG. 3C illustrates an exemplary conductive-element configuration 530 for use with various exemplary embodiments of the present disclosure;

FIG. 4 illustrates an exemplary ceramic header array for use with embodiments of the present disclosure;

FIG. 5 illustrates exemplary micro-fabricated electrode arrays for use with embodiments of the present disclosure;

FIG. 6A illustrates an exemplary implantable connector designed to connect two flexible pad arrays, for use with embodiments of the present disclosure;

FIG. 6B illustrates an exemplary implantable connector designed to connect two flexible pad arrays, for use with embodiments of the present disclosure;

FIG. 7A illustrates an exploded view of an exemplary implantable connector designed to connect a flexible pad array to a rigid pad array, for use with embodiments of the present disclosure;

FIG. 7B illustrates a collapsed view of an exemplary implantable connector designed to connect a flexible pad array to a rigid pad array, for use with embodiments of the present disclosure;

FIG. 8A illustrates an exploded view of an exemplary implantable connector designed to connect one flexible pad array to one feedthrough array of an enclosure, for use with embodiments of the present disclosure;

FIG. 8B illustrates a collapsed view of an exemplary implantable connector designed to connect one flexible pad array to one feedthrough array of an enclosure, for use with embodiments of the present disclosure;

FIG. 9A illustrates an exploded view of an exemplary implantable connector designed to connect two rigid pad arrays, for use with embodiments of the present disclosure;

FIG. 9B illustrates a collapsed view of an exemplary implantable connector designed to connect two rigid pad arrays, for use with embodiments of the present disclosure;

FIG. 10A illustrates an exploded view of an exemplary implantable connector designed to connect one rigid pad array to one feedthrough array of an enclosure for use with embodiments of the present disclosure;

FIG. 10B illustrates a collapsed view of an exemplary implantable connector designed to connect one rigid pad array to one feedthrough array of an enclosure for use with embodiments of the present disclosure;

FIGS. 11A-11C illustrate an exemplary fabrication and assembly process for an exemplary implantable connector, for use with embodiments of the present disclosure;

FIGS. 12A-12B illustrate an exemplary fabrication and assembly process for an exemplary implantable connector, for use with embodiments of the present disclosure;

FIGS. 13A-13B illustrate an exemplary fabrication and assembly process for an exemplary implantable connector, for use with embodiments of the present disclosure;

FIGS. 14A-14B illustrate an exemplary fabrication and assembly process for an exemplary implantable connector, for use with embodiments of the present disclosure;

FIGS. 15A-15B illustrate an exemplary fabrication and assembly process for an exemplary implantable connector, for use with embodiments of the present disclosure;

FIGS. 16A-16B illustrate an exemplary fabrication and assembly process for an exemplary implantable connector, for use with embodiments of the present disclosure;

FIGS. 17A-17B illustrate an exemplary fabrication and assembly process for an exemplary implantable connector, for use with embodiments of the present disclosure;

FIGS. 18A-18B illustrate an exemplary fabrication and assembly process for an exemplary implantable connector, for use with embodiments of the present disclosure;

FIGS. 19A-19B illustrate an exemplary fabrication and assembly process for an exemplary implantable connector, for use with embodiments of the present disclosure;

FIG. 20 is a block diagram of an exemplary system 20 according to various embodiments;

FIG. 21A is a schematic block diagram of a server 200 according to various embodiments; and FIG. 21B is a schematic block diagram of an exemplary mobile device 300 according to various embodiments.

DETAILED DESCRIPTION

The present disclosure more fully describes various embodiments with reference to the accompanying drawings. It should be understood that some, but not all embodiments are shown and described herein. Indeed, the embodiments may take many different forms, and accordingly this disclosure should not be construed as limited to the embodiments set forth herein. Rather, these embodiments are provided so that this disclosure will satisfy applicable legal requirements. Like numbers refer to like elements throughout.

As mentioned, various embodiments provide, as a non-limiting example, an implantable package and/or connector providing a high-channel density interconnect between high-pad-array-density interface leads and other high-pad-array-density leads or high-feedthrough-density implant headers. The implantable package and/or connector is configured for disconnecting and reconnecting with a neural interface, as needed, to change and/or upgrade electronics, batteries, or the like. Machining and micromachining are used to achieve accurate and uniform features for high channel density.

Various embodiments as described herein combine the high channel counts, high channel densities, and scalability associated with permanently bonded implants with the disconnectability and performance (i.e., reliability, channel-to-channel isolation, low contact impedance, etc.) achieved with engineered connectors conventionally known and used in the industry. To accomplish this, the production of various embodiments can combine precision machining, microfabrication processes, and larger-scale precision fabrication processes (e.g., 3-D printing, precision computer-numerical-control (CNC) machining, etc.).

The connector or implant apparatus (also referred to herein as an implant package, implantable package, and distal package) according to various embodiments comprises a first flexible pad array or a rigid pad array; a second flexible pad array, a rigid pad array, or a feedthrough array in a hermetic/nonhermetic enclosure; an isolation gasket to prevent shorting between pad array elements; an array of interconnect mechanisms to maintain reliable connections between opposing individual pads in the pad arrays; and a reliable clamping mechanism that can deliver and maintain enough constant force to achieve reliable channel-to-channel isolation and low contact impedance contact between opposing elements in the pad arrays. The isolation gasket may be made of a soft material (e.g., silicone), so it may conform to the surfaces it is clamped between. The interconnect mechanisms may be configured to have multiple points of contact, so as to achieve reliable connections that are also low-impedance and electrical in nature. The low-resistance interconnect mechanisms may be integrated within the gasket or on either flexible pad arrays, rigid pad arrays, or the feedthrough array. The low-resistance interconnect mechanisms will be compressed as the gasket is also compressed.

The clamping mechanisms, which according to certain embodiments may include a rigid top plate, a rigid bottom plate or ceramic header with base metal package, screws, and springs or other general clamping components, may be configured for achieving and reliably maintaining adequate pressure for good sealing and high electrical isolation, as well as low contact resistance.

Embodiments of the present disclosure are configured for implantation in a live subject or for one or more of submersion in marine applications, under water deployment, deployment in humid environments, deployment in well drilling or fracking environments, or deployment in environments having harsh or extremely moist conditions.

FIG. 1A illustrates an exemplary neural implant system 350 according to embodiments of the present disclosure. In embodiments, a distal package 352 is configured for implantation in a human 360 or otherwise live subject. In embodiments, the distal package 352 comprises or is in contact with one or more connectors 352B for communicably coupling via a lead 354 with an integrated electrode array 353 (i.e., the interface). In embodiments, the distal package 352 further comprises one or more connectors for communicably coupling via a lead 356 with a proximal package 355 configured to communicate with and supply power to the distal package 352. In embodiments, the proximal package 355 is configured for communication, over a communication connection 357 using one or more communication networks or protocols 358, with external remote computing apparatuses 359A, 359B . . . 359N.

FIG. 1B illustrates an exemplary neural implant system 370 according to embodiments of the present disclosure. In embodiments, an implantable package 361 is configured for implantation in a human 360 or otherwise live subject. In embodiments, implantable package 361 comprises or is in contact with one or more connectors 361B for communicably coupling via a lead 354 with an integrated electrode array 353 (i.e., the interface). In embodiments, the implant package 361 is configured for communication, over a communication connection 357 using one or more communication networks or protocols 358, with external remote computing apparatuses 359A, 359B . . . 359N.

FIG. 1C illustrates an exemplary neural implant system 380 according to embodiments of the present disclosure. In embodiments, an implantable connector 362 is configured for implantation in a human 360 or otherwise live subject. In embodiments, the implantable connector 362 is configured to provide communicable coupling between a lead 354 with an integrated electrode array 353 (i.e., the interface) and a lead 356 connected to an implant package 355. In embodiments, implant package 355 is configured for communication, over a communication connection 357 using one or more communication networks or protocols 358, with external remote computing apparatuses 359A, 359B . . . 359N.

In embodiments, implant electrodes or electrode arrays 353 are configured to transmit signals to and receive signals from neural tissue within the live subject 360. In embodiments, the connector 352B (or, in embodiments, connector 361B or connector 362) enables transmission and receipt of signals to and from the implant electrodes 353 over a conductive connection (e.g., a lead) 354.

It will be appreciated that the configurations of the exemplary neural implant systems 350, 370, 380 of FIGS. 1A-1C are yet a few examples of how the elements of the neural implant systems 350, 370, 380 may be arranged within a live subject 360. That is, the specific placement of elements of the systems as depicted in FIGS. 1A-1C is not intended to be limiting. Further, FIGS. 1A-1C provide examples of communication between those elements of the systems 350, 370, 380 and are also not intended to be limiting in any way. The elements of the neural implant systems 350, 370, 380 may be arranged throughout a body of a live or otherwise subject 360 in many configurations without departing from the scope of the present invention.

FIG. 2A illustrates an exploded view of an exemplary implantable package 352 (or, in embodiments, 361) according to various embodiments of the present disclosure. FIG. 2B illustrates a unexploded view of an exemplary implantable package 352 (or, in embodiments, 361) according to various embodiments of the present disclosure.

In certain embodiments, an implantable package 352 comprises an enclosure comprising an rigid upper plate 401, an enclosure bottom 406, and a clamping mechanism to force the rigid upper plate 401 and enclosure bottom 406 together. In embodiments, the clamping mechanism consists of a plurality of set screws 407A, 407B passing through the rigid upper plate 401. In certain embodiments, each set screw 407 is intimately surrounded by a small spring 408. It will be appreciated that, while the depiction in FIG. 2A shows two set screws in the exemplary assembly, the distal package 352 may comprise four or another number of set screws. It will further be appreciated that the clamping mechanism may be implemented in manners without one or more set screws without departing from the scope of the present disclosure.

In certain embodiments, the implantable package 352 further comprises a header substrate 405 comprising a feedthrough array (405 is also referred to herein as a feedthrough array) positioned above the enclosure bottom 406 such that at least a portion of a header substrate bottom of the header substrate 405 is hermetically sealed to the enclosure bottom 406. In embodiments, the feedthrough array comprises a plurality of feedthroughs arranged in a first array pattern.

In certain embodiments, the implantable package 352 further comprises a gasket layer 403 comprising a conductive element array 404 positioned above the header substrate 405 such that a gasket layer bottom of the gasket layer 403 is in direct contact with a header substrate top of the header substrate or feedthrough array 405. In embodiments, the conductive element array 404 comprises a plurality of conductive elements arranged in a second array pattern. In embodiments, the first array pattern matches the second array pattern such that the conductive element array 404 is aligned with and in conductive contact with the feedthrough array. In embodiments, the plurality of conductive elements fill vias in the gasket layer 403; that is, each via of an array of vias in the gasket layer 403 comprises a conductive element to form the conductive element array 404.

In certain embodiments, the implantable package 352 further comprises a flexible pad array 402 positioned above the gasket layer 403 such that a flexible pad array bottom of the flexible pad array 402 is in direct contact with a gasket layer top of the gasket layer 403. In embodiments, the flexible interface 402 comprises a micro-fabricated pad array comprising a plurality of micro-fabricated electrodes arranged in a third array pattern matching the first array pattern and the second array pattern.

In certain embodiments, the rigid upper plate 401 is positioned above the flexible pad array 402 such that the rigid upper plate bottom 401 is in direct contact with a flexible pad array top. In embodiments, the set screws 407A, 407B (and additional two set screws not shown) of the rigid upper plate top 401 are screwed into corresponding holes in the enclosure bottom 406 to clamp the rigid upper plate 401, flexible pad array 402, gasket layer 403, conductive element array 404, and header substrate 405 together. In embodiments, the clamping springs 408A, 408B (and additional two clamping springs not shown) provide a compression force required for maintaining continuous conductive contact between the flexible pad array 402, the conductive element array 404, and the feedthrough array 405.

In certain embodiments, the flexible pad array 405 enables conductive coupling to a plurality of implant electrodes 353.

In certain embodiments, the implant electrodes 353 are configured to transmit signals to and receive signals from neural tissue. In embodiments, the implantable connector 352B enables transmission of signals from the distal package 352 to the implant electrodes 353 over a conductive connection 354 (e.g., a lead) and the receipt of signals from the implant electrodes 353 to the distal package 352 over a conductive connection 354.

In certain embodiments, the implant electrodes 353 are configured to transmit signals to and receive signals from neural tissue. In embodiments, the implantable connector 352B enables transmission of signals from the implant package 361 to the implant electrodes 353 over a conductive connection 354 (e.g., a lead) and the receipt of signals from the implant electrodes 353 to the implant package 361 over a conductive connection 354.

In certain embodiments, the gasket layer 403 comprises compressible dielectric. In embodiments, the enclosure comprises metal or other high rigidity material. In embodiments, the flexible pad array 402 comprises a stack of thin polymer and metal layers (e.g., insulators and conductors).

In certain embodiments, the header substrate (or feedthrough array) 405 comprises ceramic material and has a feedthrough density of up to 11 channels per mm$^2$.

In certain embodiments, the ceramic header (or feedthrough array) 405 is a part of the enclosure bottom 406. In such embodiments, the ceramic header and enclosure bottom are hermitcally sealed together to be used as one entity.

In certain embodiments, the header substrate 405 comprises 100 or more channels.

In certain embodiments, the gasket layer 403 provides electrical isolation between neighboring conductive elements of the conductive element array 404 and the conductive solution inside the biological host 360. In embodiments, the gasket layer 403 provides a barrier from external moisture sources. In embodiments, a barrier from external moisture sources is also enabled by the clamping springs and corresponding compression force.

In certain embodiments, the distal package comprises channel-to-channel isolation of 250 KΩ or greater.

In certain embodiments, the electrical contacts between the flexible pad array elements and the feedthrough array elements have an impedance of less than 1Ω.

In certain embodiments, the conductive elements of the conductive element array 404 provide reliable low-resistance electrical connections, and may be implemented in various manners dependent upon how the distal package will be used. Distal packages that have high connection counts, which must be maintained for many years at a time, and only a few insertion cycles, are best served by a combination of multi-point contacts and the constant (or consistent) application of force (or compression force) between the connected conductive elements. For implanted applications, the connection must also be maintained despite a lack of hermeticity in the implant apparatus or connector).

It will be appreciated that the present conductive element array 404 is designed according to a need for compressible conductive elements. That is, the materials or design of the conductive elements of the conductive element array are flexible and conductive in order to achieve the desired compressibility and conductivity. FIGS. 3A-3C provide non-limiting examples of conductive element configurations.

FIG. 3A illustrates an exemplary conductive element configuration 510 for use with embodiments of the present disclosure. In embodiments, an exemplary conductive element configuration 510 comprises a plurality of conductive particles. In certain embodiments, the conductive elements comprise a mixture of compressible dielectric and conductive particles. When the gasket layer is compressed to achieve desired channel-to-channel isolation, desired vertical conduction is also achieved through the vias (i.e., conductive elements). Multi-point contact is achieved by the fact that the plurality of conductive particles are smaller than a diameter of a via, such that they can be densely packed in the via. The compressibility of the conductive particles can be aided by native elasticity of the surrounding compressible dielectric in the vias.

FIG. 3B illustrates an exemplary conductive element configuration 520 for use with embodiments of the present disclosure. In embodiments, the conductive elements 520 comprise batch-microfabricated fuzz buttons that are comprised of a bundle or mesh of conductive microwires. When the gasket layer is compressed to achieve desired channel-to-channel isolation, desired vertical conduction is also achieved through the vias (i.e., conductive elements). Multi-point contact is achieved by the fact that the plurality of conductive microwires are smaller than a diameter of a via, such that they can be densely packed in the via. The compressibility of the conductive microwires can be aided by native elasticity of the surrounding compressible dielectric in the vias.

FIG. 3C illustrates an exemplary conductive element configuration 530 for use with embodiments of the present disclosure. In certain embodiments, an exemplary conductive element configuration 530 comprises micro-fabricated springs. In certain embodiments, an exemplary conductive element configuration comprises upward-curling metal micro-cantilevers or springs. By integrating more than one cantilever or spring per feedthrough, spring-loaded multiple contact points are achieved for reliably low contact resistance.

As is discussed herein, the gasket layer of the present apparatus is critical for achieving and maintaining high channel-to-channel isolation (e.g., the impedance between neighboring flexible pad array elements and feedthrough array elements). Due to its biocompatibility, electrical insulating properties, and mechanical compressability, a silicone known as polydymethylsiloxane (PDMS) is a compressible dielectric commonly used in implants. Other biocompatible formulations of silicone and compressible polyurethane that can conform to the roughness at mating interfaces can also be used for the gasket material.

FIG. 4 illustrates an exemplary header with high-density feedthrough array for use with embodiments of the present disclosure. A header array, as shown in FIG. 4, provides high density as a two-dimensional array (as compared to in-line placement). The header array has optimal dielectric properties and is able to produce dense feedthrough arrays with reliable hermeticity. Other possible materials that could be used to form reliable implantable high-density feedthroughs include metal and silicon dioxide, conductive and dielectric silicon carbide, and conductive and dielectric diamond.

FIG. 5 illustrates exemplary micro-fabricated electrodes for use with embodiments of the present disclosure. The micro-fabricated electrodes shown in FIG. 5 may be used as an implant component for recording and stimulation (e.g., transmitting and receiving signals).

The connector configurations described herein can be used in several different embodiments to connect pad arrays of different kinds. That is, while FIGS. 2A and 2B depict a connection between a feedthrough array and a flexible pad array, it will be appreciated that neural interfaces of various kinds and combinations may be connected via connectors of the present disclosure without departing from the scope of the present disclosure. Examples are described below.

FIG. 6A illustrates an exemplary implantable connector designed to connect two flexible pad arrays (402, 420), for use with embodiments of the present disclosure. FIG. 6B illustrates an exemplary implantable connector designed to connect two flexible pad arrays (402, 420), for use with embodiments of the present disclosure. An exemplary implantable connector may comprise a rigid lower plate 421 and a rigid upper plate 401. It will be appreciated that the rigid lower plate 421 may be a part of, separate from, or in addition to a rigid bottom enclosure 406 as depicted in FIGS. 2A and 2B.

FIG. 7A illustrates an exemplary implantable connector designed to connect a flexible pad array (402) to a rigid pad array (422), for use with embodiments of the present disclosure. FIG. 7B illustrates an exemplary implantable connector designed to connect a flexible pad array (402) to a rigid pad array (422), for use with embodiments of the present disclosure. An exemplary implantable connector may comprise a rigid lower plate 421.

FIG. 8A illustrates an exemplary implantable connector designed to connect one flexible pad array (402) to one feedthrough array (405) of an enclosure, for use with embodiments of the present disclosure. FIG. 8B illustrates an exemplary implantable connector designed to connect one flexible pad array (402) to one feedthrough array (405) of an enclosure, for use with embodiments of the present disclosure.

In various embodiments, an exemplary implantable connector may comprise a rigid lower plate 421.

FIG. 9A illustrates an exemplary implantable connector designed to connect two rigid pad arrays (423, 422), for use with embodiments of the present disclosure. FIG. 9B illustrates an exemplary implantable connector designed to connect two rigid pad arrays (423, 422), for use with embodiments of the present disclosure. An exemplary implantable connector may comprise a rigid lower plate 421.

FIG. 10A illustrates an exemplary implantable connector designed to connect one rigid pad array (423) to one feedthrough array (405) of an enclosure for use with embodiments of the present disclosure. FIG. 10B illustrates an exemplary implantable connector designed to connect one rigid pad array (423) to one feedthrough array (405) of an enclosure for use with embodiments of the present disclosure.

Different fabrication and assembly processes and can be used to produce connectors of each of the embodiments described herein. Examples are discussed below.

An exemplary fabrication and assembly process used to produce an exemplary connector assembly begins with the production of the constituent components.

In embodiments, an assembly process comprises fabricating an rigid upper plate 401 and lower plate/enclosure 406 for an implant apparatus disclosed herein. These components are made of metal and produced with precision machining processes. However, other materials (e.g., ceramic, glass, etc.) and fabrication processes (e.g., microfabrication, laser processing, etc.) can be used to form the upper plate 401 and lower plate/enclosure 406.

Next, the lower contact array 405 is produced. This lower contact or feedthrough array can be made of ceramic and metal as well as other combinations of dielectric and conductor (e.g., glass and metal, conductive silicon carbide and insulating silicon carbide, insulating diamond and conductive diamond, etc.). For the configuration for an implant connector 361B, the lower array can be microfabricated from of a stack of thin layers of dielectric and metal, such as polyimide and platinum and other materials.

The flexible pad array 402 that the rigid upper plate 401 presses down upon can also be microfabricated from of a stack of thin layers of dielectric and metal, such as polyimide and platinum and other materials.

The gasket 403 clamped between a flexible pad array 402 bottom and a feedthrough header 405 top or lower flexible pad array 422 top is made out of a compressible dielectric. Examples of compressible dielectrics used for the gasket 403 include forms of silicone (e.g., PDMS) and polyurethane. The gasket 403 can be fabricated with conventional molding processes, microfabrication (e.g., spin-on) processes, laser processing, precision machining processes, etc.

Since there are multiple designs for the conductive element array 404, it can be produced with different processes and out of different materials. One design for the conductive element array 404 is to use conductive particles imbedded into an elastic material. The composite of conductive particles and elastic materials can be produced with different processes. An exemplary process injects a mixture of conductive particles and elastic material into holes in the gasket 403 located directly below each element in the flexible pad array. Another exemplary process integrates the mixture of conductive particles into a continuous layer of the elastic material of the gasket 403. Another exemplary process uses conductive microwires instead of microparticles to form the elements in the conductive element array 404. The microwires can be produced with a process that forms a dense interconnected mat of eletrospun polymer microfibers. Photolithography can be used to pattern the interconnected mat of microfibers into an array of small cylinders of interconnected microfibers segments. Subsequent anaerobic high temperature process uses pyrolysis to convert the polymer material into a conductive pyrolytic carbon material. The resulting cylinders of interconnected conductive pyrolytic microfibers can be fabricated onto a feedthrough array top 405 or a flexible pad array bottom 402, or into the gasket 403 itself. The screws through the upper plate and the springs surrounding each screen can be produced with convention precision machining processes.

The assembly process begins with the base plate 406, to which the feedthrough array may be permanently affixed. The process for attachment or integration depends on the materials used (e.g., brazing for ceramic and metal, laser processing for glass and metal, microfabrication for metal-polymer layers, etc.). For the case of an implant connector with lower flexible pad array, it is aligned to the base place with machined or micromachined mechanical guides (e.g., guide pins, etc.). Next the gasket and the conductive element array is aligned to and attached to the lower assembled parts. Similarly, the flexible pad array and the upper plate are also aligned to the lower assembled parts. The screws, springs, and the upper plate can be preassembled prior to alignment and assembly with the lower assembled parts. Finally, the screws can be turned to tighten the parts together, compress the gasket, and complete the implantable connector assembly process.

FIGS. 11A-11C illustrate an exemplary fabrication and assembly process for an exemplary implantable connector, for use with embodiments of the present disclosure. In FIG. 11A, the gasket 403 is formed separately on a temporary substrate 424 and then removed from the temporary substrate. In FIG. 11B the gasket is assembled onto a feedthrough array 405 and the conductive elements 404 are then integrated into the holes in the gasket and on the top surface of the pads in the feedthrough array. In FIG. 11C, an upper pad array is then aligned and the connector assembly is clamped together by an exemplary clamping mechanism, in this case consisting of a rigid upper plate 401, screws 407, springs 408, and an enclosure bottom 406.

FIGS. 12A-12B illustrate an exemplary fabrication and assembly process for an exemplary implantable connector, for use with embodiments of the present disclosure. In FIG. 12A, the gasket 403 is formed separately on a temporary substrate 424 and the conductive elements 404 are then integrated into the holes of the gasket. The gasket with integrated conductive elements is then removed from the temporary substrate. In FIG. 12B, the gasket with integrated conductive elements is then aligned to an upper pad array 402 and a feedthrough array 405. The connector assembly is clamped together by an exemplar clamping mechanism, in this case consisting of a rigid upper plate 401, screws 407, springs 408, and an enclosure bottom 406.

FIGS. 13A-13B illustrate an exemplary fabrication and assembly process for an exemplary implantable connector, for use with embodiments of the present disclosure. In FIG. 13A, the gasket 403 is formed separately on a temporary substrate 424 and then removed from the temporary substrate. The conductive elements 404 are integrated onto the pads of a feedthrough array 405. In FIG. 13B, the gasket is then aligned to an upper pad array 402 and a feedthrough array 405 with integrated conductive elements 404. The connector assembly is then clamped together by an exemplar clamping mechanism, in this case consisting of a rigid upper plate 401, screws 407, springs 408, and an enclosure bottom 406.

FIGS. 14A-14B illustrate an exemplary fabrication and assembly process for an exemplary implantable connector, for use with embodiments of the present disclosure. In FIG. 14A, the conductive elements 404 are formed on a temporary substrate 424 The gasket 403 is integrated with the conductive elements on the temporary substrate. The gasket with integrated conductive elements is then removed from the temporary substrate. In FIG. 14B the gasket with integrated conductive elements is assembled between an upper pad array 402 and a feedthrough array 405 and the connector assembly is then clamped together by an exemplar clamping mechanism, in this case consisting of a rigid upper plate 401, screws 407, springs 408, and an enclosure bottom 406.

FIGS. 15A-15B illustrate an exemplary fabrication and assembly process for an exemplary implantable connector, for use with embodiments of the present disclosure. In FIG. 15A, the gasket 403 is formed simultaneously with integrated conductive elements 404 on a temporary substrate 424 and the gasket with integrated conductive elements is then removed from a temporary substrate. In FIG. 15B the gasket with integrated conductive elements is assembled between an upper pad array 402 and a feedthrough array 405 and the connector assembly is then clamped together by an exemplar clamping mechanism, in this case consisting of a rigid upper plate 401, screws 407, springs 408, and an enclosure bottom 406.

FIGS. 16A-16B illustrate an exemplary fabrication and assembly process for an exemplary implantable connector, for use with embodiments of the present disclosure. In FIG. 16A. the gasket 403 is formed on a lower flexible pad array 420 and conductive elements 404 are then integrated into the holes in the gasket. In FIG. 16B, the lower flexible pad array with integrated gasket and conductive elements is then assembled with a upper flexible pad array 402 and the connector assembly is then clamped together by an exemplar clamping mechanism, in this case consisting of a rigid upper plate 401, screws 407, springs 408, and a lower rigid plate 421.

FIGS. 17A-17B illustrate an exemplary fabrication and assembly process for an exemplary implantable connector, for use with embodiments of the present disclosure. In FIG. 17A, the conductive elements 404 are formed onto the metal pads of a lower flexible pad array 420. A gasket is then formed on the lower flexible pad array with integrated conductive elements. In FIG. 17B, the lower flexible pad array with integrated gasket and conductive elements is then assembled with an upper flexible pad array 402 and the connector assembly is then clamped together by an exemplar clamping mechanism, in this case consisting of a rigid upper plate 401, screws 407, springs 408, and a lower rigid plate 421.

FIGS. 18A-18B illustrate an exemplary fabrication and assembly process for an exemplary implantable connector, for use with embodiments of the present disclosure. In FIG. 18A, the gasket 403 is formed simultaneously with integrated conductive elements 404 on a lower flexible pad array 420. In FIG. 18B, the lower flexible pad array with integrated gasket and conductive elements is then assembled with an upper flexible pad array 402 and the connector assembly is then clamped together by an exemplar clamping mechanism, in this case consisting of a rigid upper plate 401, screws 407, springs 408, and a lower rigid plate 421.

FIGS. 19A-19B illustrate an exemplary fabrication and assembly process for an exemplary implantable connector, for use with embodiments of the present disclosure. In certain embodiments, an optional elastic sheet 409 is positioned either in between the rigid bottom plate 421 and lower pad array 420 or in between upper pad array 402 and upper rigid plate 401 or both such that the elastic sheet 409 is in direct contact with the abovementioned parts. In FIGS. 19A and 19B, 409 is positioned between 420 and 421. In embodiments, the elastic sheet 409 compensates for nonuniform force distribution applied during clamping. This provides better and equal isolation in every area/side/corner of the gasket.

In embodiments, the flexible dielectric sheet 409 is used in many other embodiments of the present disclosure. In embodiments, the flexible dielectric sheet 409 comprises similar or the same material used for the gasket (403).

A variety of materials and fabrication processes can be used to form the flexible pad arrays, the rigid pad arrays, and the feedthrough array integrated into the enclosures.

Non-limiting examples of conductive materials for flexible pad arrays for use with embodiments of the present disclosure include conductive inorganic materials (e.g., metals such as platinum, platinum grey, platinum black, gold, silver, copper, titanium, TiN, IrOx) formed in a continuous film or a stretchable film), conductive organic materials (e.g., conductive polymers, poly(3,4-ethylenedioxythiophene)-poly(styrenesulfonate) (PEDOT:PSS), polypyrole, graphene, pyrolyzed polymer films or fibers that could also be metalized, carbon nanotubes, graphene, doped ultra-nanocrystalline diamond, doped silicon carbide, and the like), or conductive silicones (e.g. silicone packed with a dense arrangement of conductive particles, and the like).

Non-limiting examples of materials for use as dielectrics for flexible pad arrays for use with embodiments of the present disclosure include insulating inorganic materials (e.g., silicon dioxide ($SiO_2$), silicon nitride ($Si_xN_y$), silicon carbide (SiC), diamond-like carbon, ultra-nanocrystalline diamond, etc.), insulating organic materials (polymers (e.g., polyimides, parylenes, polyurethanes, liquid crystal polymers (LCP), polyether ether ketone (PEEK), and the like)), and insulating silicones (e.g., polydimethysiloxane (PDMS).

Non-limiting examples of methodologies or processes for use in manufacturing flexible pad arrays for use with embodiments of the present disclosure include photolithography, screen printing, 3-D printing, physical vapor deposition, chemical vapor deposition, atomic layer deposition, laser ablation, electroless plating, electroplating, spin coating, spray coating, electrospinning, and the like.

Non-limiting examples of conductive materials for rigid pad arrays for use with embodiments of the present disclosure include conductive inorganic materials (e.g., metals such as platinum, platinum grey, platinum black, gold, silver, copper, titanium, TiN, IrOx) formed in a continuous film, a wire, or dense arrangement of particles, and conductive organic materials (e.g., conductive polymers, poly(3,4-ethylenedioxythiophene)-poly(styrenesulfonate) (PEDOT:PSS), polypyrole, graphene, pyrolyzed polymer films or fibers that could also be metalized, carbon nanotubes, graphene, doped ultra-nanocrystalline diamond, doped silicon carbide, and the like).

Non-limiting examples of materials for use as dielectrics for rigid pad arrays for use with embodiments of the present disclosure include insulating inorganic materials (e.g., silicon dioxide ($SiO_2$), silicon nitride ($Si_xN_y$), silicon carbide (SiC), diamond-like carbon, ultra-nanocrystalline diamond, ceramics, high-temperature co-fired ceramic (HTCC), low-temperature co-fired ceramic (LTCC), and the like), insulating polymers (e.g., printed-circuit-board (PCB) dielectric laminates, polyimides, parylene, polyurethane, liquid crystal polymers (LCP), polyether ether ketone (PEEK), and the like), and insulating silicones (e.g., polydimethysiloxane (PDMS), and the like).

Non-limiting examples of materials for use as rigid substrates for rigid pad arrays for use with embodiments of the present disclosure include rigid substrates (e.g., printed-circuit-board (PCB) dielectric laminates, silicon, glass, ceramic (HTCC, LTCC etc.), metal, and the like).

Non-limiting examples of methodologies or processes for use in manufacturing rigid pad arrays for use with embodiments of the present disclosure include photolithography, screen printing, 3-D printing, physical vapor deposition, chemical vapor deposition, atomic layer deposition, laser ablation, electroless plating, electroplating, spin coating, spray coating, electrospinning, etc.), thermal diffusion, ion implantation, chemical mechanical polishing (CMP), thermocompression bonding, eutectic bonding, soldering, brazing, laser bonding, thermal lamination, thermal compression, sintering, single-crystal-silicon growth, drawn molten silica, cast molten silica, and the like.

Non-limiting examples of conductive materials for feedthrough arrays for use with embodiments of the present disclosure include conductive inorganic materials (e.g., metals such as platinum, gold, silver, copper) formed in a continuous material or dense arrangement of particles.

Non-limiting examples of materials for use as dielectrics for feedthrough arrays for use with embodiments of the present disclosure include insulating inorganic materials (e.g., high-temperature co-fired ceramic (HTCC), low-temperature co-fired ceramic (LTCC), glass, silicon carbide (SiC), and ultra-nanocrystalline diamond).

Non-limiting examples of methodologies or processes for use in manufacturing feedthrough arrays for use with embodiments of the present disclosure include screen printing, 3-D printing, electroless plating, electroplating, thermocompression bonding, eutectic bonding, brazing, sintering, chemical mechanical polishing (CMP), mechanical punch, laser etching, deep reactive ion etching, and the like.

Non-limiting examples of materials for gaskets for use with embodiments of the present disclosure include silicones (e.g., polydimethysiloxane (PDMS) and the like), and polymers (e.g., high-density polyethylene (HDPE), low-density polyethylene (LPDE), polytetrafluoroethylene (PTFE), polyurethanes, polyether ether ketone polyether ether ketone (PEEK), and the like).

Non-limiting examples of methodologies or processes for use in manufacturing gaskets for use with embodiments of the present disclosure include photolithography, soft lithography, die punching, casting, injection molding, laser etching, screen printing, 3-D printing, spin coating, spray coating, and the like.

Non-limiting examples of materials for conductive elements (e.g., a cantilever type conductive element) for use with embodiments of the present disclosure include high coefficient of thermal expansion (CTE) materials (e.g., metals such as platinum, gold, silver, copper, titanium, tungsten, chromium, and the like) and low CTE materials (e.g., silicon, silicon dioxide ($SiO_2$), silicon nitride ($Si_xN_y$), silicon carbide (SiC), and the like).

Non-limiting examples of methodologies or processes for use in manufacturing conductive elements (e.g., a cantilever type conductive element) for use with embodiments of the present disclosure include photolithography, physical vapor deposition, chemical vapor deposition, atomic layer deposition, laser ablation, electroless plating, electroplating, spin coating, spray coating, annealing, diffusion, ion implantation, wet and dry etching, screen printing, and 3-D printing.

Non-limiting examples of materials for conductive elements (e.g., a fuzz button type conductive element) for use with embodiments of the present disclosure include conductive organic materials (e.g., pyrolyzed polymer, conductive polymer, carbon nanotubes, graphene, and the like) and conductive inorganic materials (e.g., platinum, gold, silver, copper, nickel, and the like).

Non-limiting examples of methodologies or processes for use in manufacturing conductive elements (e.g., a fuzz button type conductive element) for use with embodiments of the present disclosure include photolithography, spin coating, electrospinning, pyrolysis, electroplating, electroless plating, wet and dry etching and 3-D printing.

Non-limiting examples of materials for conductive elements (e.g., using particles) for use with embodiments of the present disclosure include conductive inorganic materials (e.g., gold, platinum, silver, copper, nickel, and the like), conductive organic materials (e.g., conducive polymers, poly(3,4-ethylenedioxythiophene)-poly(styrenesulfonate) (PEDOT:PSS), polypyrole, carbon nanotubes, graphene, and the like), silicones (e.g., polydimethysiloxane (PDMS) and the like), and polymers (e.g., high-density polyethylene (HDPE), low-density polyethylene (LPDE), polytetrafluoroethylene (PTFE), polyurethanes, polyether ether ketone polyether ether ketone (PEEK), polystyrene, and the like).

Non-limiting examples of methodologies or processes for use in manufacturing conductive elements (e.g., using particles) for use with embodiments of the present disclosure include microfluidic synthesis, decomposition synthesis, electroplating, electroless plating, screen printing, 3-D printing, photolithography, spin coating, spray coating, and the like.

Non-limiting examples of materials for clamping mechanisms and springs for use with embodiments of the present disclosure include metals (e.g., titanium, aluminum, stainless steel, and the like). It will be appreciated that materials for springs may exhibit a significantly lower creep than those materials for use as gaskets described herein.

Non-limiting examples of methodologies or processes for use in manufacturing clamping mechanisms and springs for use with embodiments of the present disclosure include manufacturing processes (e.g., milling, drilling, turning, routing, casting, molding, pressing, and the like), polishing (e.g., lapping, honing, chemical, and the like) and additive manufacturing (e.g., 3D printing, and the like).

Non-limiting examples of materials for enclosures for use with embodiments of the present disclosure include metals (e.g., titanium, aluminum, stainless steel), ceramics (e.g., alumina, etc.), insulators (e.g., glass, sapphire, etc.), polymers (e.g., epoxy, polyurethanes, liquid crystal polymer (LCP), high-density polyethylene (HDPE), low-density polyethylene (LPDE), polytetrafluoroethylene (PTFE), etc.).

Non-limiting examples of methodologies or processes for use in manufacturing enclosures for use with embodiments of the present disclosure include manufacturing processes (e.g., milling, drilling, turning, routing, casting, molding, pressing, etc.), sheet-metal processing (forming, bending, punching, drawing, etc.) polishing (e.g., lapping, honing, chemical, etc.) and additive manufacturing (e.g., 3D printing, etc.), bonding processes (e.g., thermocompression, anodic, etc.), and brazing.

Exemplary Apparatuses, Methods, Systems, Computer Program Products, & Computing Entities Embodiments as described herein may also be implemented in various ways, including as or incorporating components of computer program products. A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM)), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, micro secure digital (microSD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory VRAM, cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. However, embodiments of the present invention may also take the form of an entirely hardware embodiment performing certain steps or operations.

Various embodiments are described below with reference to block diagrams and flowchart illustrations of apparatuses, methods, systems, and computer program products. It should be understood that each block of any of the block diagrams and flowchart illustrations, respectively, may be implemented in part by computer program instructions, e.g., as logical steps or operations executing on a processor in a computing system. These computer program instructions may be loaded onto a computer, such as a special purpose computer or other programmable data processing apparatus to produce a specifically-configured machine, such that the instructions which execute on the computer or other programmable data processing apparatus implement the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the functionality specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide operations for implementing the functions specified in the flowchart block or blocks.

Accordingly, blocks of the block diagrams and flowchart illustrations support various combinations for performing the specified functions, combinations of operations for performing the specified functions and program instructions for performing the specified functions. It should also be understood that each block of the block diagrams and flowchart illustrations, and combinations of blocks in the block diagrams and flowchart illustrations, could be implemented by special purpose hardware-based computer systems that perform the specified functions or operations, or combinations of special purpose hardware and computer instructions.

Exemplary Architecture of System 20

FIG. 20 is a block diagram of an exemplary system 20 that can be used in conjunction with various embodiments described herein. In at least the illustrated embodiment, the system 20 may include one or more central computing devices 110, one or more distributed computing devices 120, and one or more distributed handheld or mobile devices 300, all configured in communication with a central server 200 via one or more networks 130. While FIG. 20 illustrates the various system entities as separate, standalone entities, the various embodiments are not limited to this particular architecture.

According to various embodiments, the one or more networks 130 may be capable of supporting communication in accordance with any one or more of a number of second-generation (2G), 2.5G, third-generation (3G), and/or fourth-generation (4G) mobile communication protocols, or the like. More particularly, the one or more networks 130 may be capable of supporting communication in accordance with 2G wireless communication protocols IS-136 (TDMA), GSM, and IS-95 (CDMA). Also, for example, the one or more networks 130 may be capable of supporting communication in accordance with 2.5G wireless communication protocols GPRS, Enhanced Data GSM Environment (EDGE), or the like. In addition, for example, the one or more networks 130 may be capable of supporting communication in accordance with 3G wireless communication protocols such as Universal Mobile Telephone System (UMTS) network employing Wideband Code Division Multiple Access (WCDMA) radio access technology. Some narrow-band AMPS (NAMPS), as well as TACS, network(s) may also benefit from embodiments of the present invention, as should dual or higher mode mobile stations (e.g., digital/analog or TDMA/CDMA/analog phones). As yet another example, each of the components of the system 5 may be configured to communicate with one another in accordance with techniques such as, for example, radio frequency (RF), Bluetooth™ infrared (IrDA), or any of a number of different wired or wireless networking techniques, including a wired or wireless Personal Area Network ("PAN"), Local Area Network ("LAN"), Metropolitan Area Network ("MAN"), Wide Area Network ("WAN"), or the like.

Although the device(s) 110-300 are illustrated in FIG. 20 as communicating with one another over the same network 130, these devices may likewise communicate over multiple, separate networks.

According to one embodiment, in addition to receiving data from the server 200, the distributed devices 110, 120, and/or 300 may be further configured to collect and transmit data on their own. In various embodiments, the devices 110, 120, and/or 300 may be capable of receiving data via one or more input units or devices, such as a keypad, touchpad, barcode scanner, radio frequency identification (RFID) reader, interface card (e.g., modem, etc.) or receiver. The devices 110, 120, and/or 300 may further be capable of storing data to one or more volatile or non-volatile memory modules, and outputting the data via one or more output units or devices, for example, by displaying data to the user operating the device, or by transmitting data, for example over the one or more networks 130.

Exemplary Server 200

In various embodiments, the server 200 may include various systems for performing one or more functions in accordance with various embodiments of the present invention, including those more particularly shown and described herein. It should be understood, however, that the server 200 might include a variety of alternative devices for performing one or more like functions, without departing from the spirit and scope of the present invention. For example, at least a portion of the server 200, in certain embodiments, may be located on the distributed device(s) 110, 120, and/or the handheld or mobile device(s) 300, as may be desirable for particular applications. As will be described in further detail below, in at least one embodiment, the handheld or mobile device(s) 300 may contain one or more mobile applications 330 which may be configured so as to provide a user interface for communication with the server 200, all as will be likewise described in further detail below.

FIG. 21A is a schematic diagram of the server 200 according to various embodiments. The server 200 includes a processor 230 that communicates with other elements within the server via a system interface or bus 235. Also included in the server 200 is a display/input device 250 for receiving and displaying data. This display/input device 250 may be, for example, a keyboard or pointing device that is used in combination with a monitor. The server 200 further includes memory 220, which preferably includes both read only memory (ROM) 226 and random access memory (RAM) 222. The server's ROM 226 is used to store a basic input/output system 224 (BIOS), containing the basic routines that help to transfer information between elements within the server 200. Various ROM and RAM configurations have been previously described herein.

In addition, the server 200 includes at least one storage device or program storage 210, such as a hard disk drive, a floppy disk drive, a CD Rom drive, or optical disk drive, for storing information on various computer-readable media, such as a hard disk, a removable magnetic disk, or a CD-ROM disk. As will be appreciated by one of ordinary skill in the art, each of these storage devices 210 are connected to the system bus 235 by an appropriate interface. The storage devices 210 and their associated computer-readable media provide nonvolatile storage for a personal computer. As will be appreciated by one of ordinary skill in the art, the computer-readable media described above could be replaced by any other type of computer-readable media known in the art. Such media include, for example, magnetic cassettes, flash memory cards, digital video disks, and Bernoulli cartridges.

Although not shown, according to an embodiment, the storage device 210 and/or memory of the server 200 may further provide the functions of a data storage device, which may store historical and/or current delivery data and delivery conditions that may be accessed by the server 200. In this regard, the storage device 210 may comprise one or more databases. The term "database" refers to a structured collection of records or data that is stored in a computer system, such as via a relational database, hierarchical database, or network database and as such, should not be construed in a limiting fashion.

A number of program modules (e.g., exemplary modules 400-700) comprising, for example, one or more computer-readable program code portions executable by the processor 230, may be stored by the various storage devices 210 and within RAM 222. Such program modules may also include an operating system 280. In these and other embodiments, the various modules 400, 500, 600, 700 control certain aspects of the operation of the server 200 with the assistance of the processor 230 and operating system 280. In still other embodiments, it should be understood that one or more additional and/or alternative modules may also be provided, without departing from the scope and nature of the present invention.

In various embodiments, the program modules 400, 500, 600, 700 are executed by the server 200 and are configured to generate one or more graphical user interfaces, reports, instructions, and/or notifications/alerts, all accessible and/or transmittable to various users of the system 20. In certain embodiments, the user interfaces, reports, instructions, and/ or notifications/alerts may be accessible via one or more networks 130, which may include the Internet or other feasible communications network, as previously discussed.

In various embodiments, it should also be understood that one or more of the modules 400, 500, 600, 700 may be alternatively and/or additionally (e.g., in duplicate) stored locally on one or more of the devices 110, 120, and/or 300 and may be executed by one or more processors of the same. According to various embodiments, the modules 400, 500, 600, 700 may send data to, receive data from, and utilize data contained in one or more databases, which may be comprised of one or more separate, linked and/or networked databases.

Also located within the server 200 is a network interface 260 for interfacing and communicating with other elements of the one or more networks 130. It will be appreciated by one of ordinary skill in the art that one or more of the server 200 components may be located geographically remotely from other server components. Furthermore, one or more of the server 200 components may be combined, and/or additional components performing functions described herein may also be included in the server.

While the foregoing describes a single processor 230, as one of ordinary skill in the art will recognize, the server 200 may comprise multiple processors operating in conjunction with one another to perform the functionality described herein. In addition to the memory 220, the processor 230 can also be connected to at least one interface or other means for displaying, transmitting and/or receiving data, content or the like. In this regard, the interface(s) can include at least one communication interface or other means for transmitting and/or receiving data, content or the like, as well as at least one user interface that can include a display and/or a user input interface, as will be described in further detail below.

The user input interface, in turn, can comprise any of a number of devices allowing the entity to receive data from a user, such as a keypad, a touch display, a joystick or other input device.

Still further, while reference is made to the "server" 200, as one of ordinary skill in the art will recognize, embodiments of the present invention are not limited to traditionally defined server architectures. Still further, the system of embodiments of the present invention is not limited to a single server, or similar network entity or mainframe computer system. Other similar architectures including one or more network entities operating in conjunction with one another to provide the functionality described herein may likewise be used without departing from the spirit and scope of embodiments of the present invention. For example, a mesh network of two or more personal computers (PCs), similar electronic devices, or handheld portable devices, collaborating with one another to provide the functionality described herein in association with the server 200 may likewise be used without departing from the spirit and scope of embodiments of the present invention.

According to various embodiments, many individual steps of a process may or may not be carried out utilizing the computer systems and/or servers described herein, and the degree of computer implementation may vary, as may be desirable and/or beneficial for one or more particular applications.

Distributed Handheld (or Mobile) Device(s) 300

FIG. 21B provides an illustrative schematic representative of a mobile device 300 that can also and/or alternatively be used in conjunction with various embodiments as described herein. Mobile devices 300 can be operated by various parties. As shown in FIG. 21B, a mobile device 300 may include an antenna 312, a transmitter 304 (e.g., radio), a receiver 306 (e.g., radio), and a processing element 308 that provides signals to and receives signals from the transmitter 304 and receiver 306, respectively.

The signals provided to and received from the transmitter 304 and the receiver 306, respectively, may include signaling data in accordance with an air interface standard of applicable wireless systems to communicate with various entities, such as the server 200, the distributed devices 110, 120, and/or the like. In this regard, the mobile device 300 may be capable of operating with one or more air interface standards, communication protocols, modulation types, and access types. More particularly, the mobile device 300 may operate in accordance with any of a number of wireless communication standards and protocols. In a particular embodiment, the mobile device 300 may operate in accordance with multiple wireless communication standards and protocols, such as GPRS, UMTS, CDMA2000, 1xRTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the mobile device 300 may according to various embodiments communicate with various other entities using concepts such as Unstructured Supplementary Service data (USSD), Short Message Service (SMS), Multimedia Messaging Service (MMS), Dual-Tone Multi-Frequency Signaling (DTMF), and/or Subscriber Identity Module Dialer (SIM dialer). The mobile device 300 can also download changes, add-ons, and updates, for instance, to its firmware, software (e.g., including executable instructions, applications, program modules), and operating system.

According to one embodiment, the mobile device 300 may include a location determining device and/or functionality. For example, the mobile device 300 may include a GPS module adapted to acquire, for example, latitude, longitude, altitude, geocode, course, and/or speed data. In one embodiment, the GPS module acquires data, sometimes known as ephemeris data, by identifying the number of satellites in view and the relative positions of those satellites.

The mobile device 300 may also comprise a user interface (that can include a display 316 coupled to a processing element 308) and/or a user input interface (coupled to a processing element 308). The user input interface can comprise any of a number of devices allowing the mobile device 300 to receive data, such as a keypad 318 (hard or soft), a touch display, voice or motion interfaces, or other input device. In embodiments including a keypad 318, the keypad can include (or cause display of) the conventional numeric (0-9) and related keys (#, *), and other keys used for operating the mobile device 300 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The mobile device 300 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database mapping systems, data, applications, programs, program modules, scripts, source code, object code, byte code, compiled code, interpreted code, machine code, executable instructions, and/or the like to implement the functions of the mobile device 300.

The mobile device 300 may also include one or more of a camera 326 and a mobile application 330. The camera 326 may be configured according to various embodiments as an additional and/or alternative data collection feature, whereby one or more items may be read, stored, and/or transmitted by the mobile device 300 via the camera. The mobile application 330 may further provide a feature via which various tasks may be performed with the mobile device 300. Various configurations may be provided, as may be desirable for one or more users of the mobile device 300 and the system 20 as a whole.

Various Embodiments

In many embodiments of the present disclosure, an apparatus. comprises a lower plate and a lower pad array comprising a plurality of lower pads, each lower pad arranged in a first pattern and the lower pad array positioned above the lower plate. In many of these embodiments, the apparatus further comprises a gasket layer positioned above the lower pad array. In many of these embodiments, the apparatus further comprises a conductive element array comprising a plurality of conductive elements, each conductive element arranged in a second pattern, the conductive element array positioned above the lower pad array. In many of these embodiments, the apparatus further comprises an upper pad array comprising a plurality of upper pads, each upper pad arranged in a third pattern, the upper pad array positioned above the conductive element array. In many of these embodiments, the apparatus further comprises an upper plate and a clamping mechanism that enables the lower plate, lower pad array, gasket layer, conductive element array, upper pad array, and upper plate to be compressed together.

In many of these embodiments, the lower pad array is positioned above the lower plate such that a lower pad array bottom is in direct contact with a lower plate top. In many of these embodiments, the gasket layer is positioned above the lower pad array such that a gasket layer bottom is in direct contact with a lower pad array top. In many of these embodiments, the upper pad array is positioned above the gasket layer such that an upper pad array bottom is in direct contact with a gasket layer top. In many of these embodiments, the upper plate is positioned above the upper pad array such that an upper plate bottom is in direct contact with an upper pad array top. In many of these embodiments, the conductive element array is positioned above the lower pad array such that a conductive element array bottom is in direct contact with a lower pad array top.

In many of these embodiments, the conductive element array is positioned below the upper pad array such that a conductive element array top is in direct contact with an upper pad array bottom. In many of these embodiments, the first pattern matches the second pattern such that the conductive element array is aligned with and in conductive contact with the lower pad array. In many of these embodiments, the second pattern matches the third pattern such that the upper pad array is aligned with and in conductive contact with the conductive element array. In many of these embodiments, the clamping mechanism provides a compression force needed to reliably maintain continuous conductive contact between the upper pad array and the lower pad array. In many of these embodiments, the clamping mechanism provides a compression force needed to reliably maintain continuous compression of the gasket layer to electrically isolate each individual vertically connected set of lower pad array element, conductive element, and upper pad array element.

In many of these embodiments, the upper plate and the upper pad array are integrated into a combined upper element. In many of these embodiments, the lower plate and the lower pad array are integrated into a combined lower element. In many of these embodiments, the gasket layer comprises one of a anisotropic conductive elastomer or a compressible dielectric elastic. In many of these embodiments, the clamping mechanism comprises one or more of elastic force generation elements or elastic elements. In many of these embodiments, the force generation elements comprise one or more of a plurality of screws, a plurality of nuts, or a plurality of washers. In many of these embodiments, the elastic elements comprise springs. In many of these embodiments, the plurality of screws pass through the upper plate and end inside the lower plate, and are optionally secured by a plurality of nuts and washers.

In many of these embodiments, the upper pad array comprises a composite of conductive and dielectric materials. In many of these embodiments, the lower pad array comprises a composite of conductive and dielectric materials. In many of these embodiments, the upper plate is rigid.

In many of these embodiments, the lower plate is rigid. In many of these embodiments, the lower pad array is one of flexible or rigid.

In many of these embodiments, the lower plate comprises an enclosure and the lower pad array comprises a feedthrough array that enables conductive coupling between an inside of the enclosure, conductive elements in the gasket layer, and the upper pad array. In many of these embodiments, the upper pad array is one of flexible or rigid. In many of these embodiments, one or more of the upper pad array or lower pad array is part of an interface lead that routes electrical traces to one of electrodes or implanted electrodes. In many of these embodiments, one or more of the upper pad array or lower pad array is part of a lead that routes electrical traces to electronics. In many of these embodiments, one or more of the upper pad array or lower pad array comprises a feed through array that routes electrical signals to electronics inside one of an enclosure or an implanted enclosure. In many of these embodiments, the interface lead is configured to transmit signals to and receive signals from neural tissue or another signal source. In many of these embodiments, the conductive elements comprise one or more of a plurality of micro-fabricated springs, a plurality of metallic micro-particles, or a plurality of metallic micro-wires. In many of these embodiments, the conductive elements are fabricated as an integral part of the lower pad array. In many of these embodiments, the conductive elements are fabricated as an integral part of the upper pad array.

In many of these embodiments, the conductive elements are fabricated as an integral part of the lower pad array and the upper pad array. In many of these embodiments, the conductive elements are fabricated as an integral part of one or more of the feedthrough array or the gasket layer.

In many of these embodiments, the apparatus is configured for disconnecting and reconnecting with a neural interface to change and/or upgrade electronics, or batteries.

In many of these embodiments, one or more of the upper plate or lower plate comprises metal, ceramic, glass, or polymer material. In many of these embodiments, the feedthrough array comprises one or more of ceramic, glass, semiconductor, or polymer material. In many of these embodiments, the gasket layer comprises compressible dielectric polymer, silicone, polydimethylsiloxane (PDMS), or polyurethane. In many of these embodiments, one or more of the first pattern, the second pattern, or the third pattern comprises an array pattern.

In many embodiments of the present disclosure, a method of manufacturing an apparatus comprises positioning a lower pad array above a lower plate, the lower pad array comprising a plurality of lower pads, each lower pad arranged in a first pattern. In many of these embodiments, the method further comprises positioning a gasket layer above the lower pad array. In many of these embodiments, the method further comprises positioning a conductive element array above the lower pad array, the conductive element array comprising a plurality of conductive elements, each conductive element arranged in a second pattern. In many of these embodiments, the method further comprises positioning an upper pad array above the conductive element array, the upper pad array comprising a plurality of upper pads, each upper pad arranged in a third pattern. In many of these embodiments, the method further comprises positioning an upper plate above the upper pad array. In many of these embodiments, the method further comprises compressing the lower plate, lower pad array, gasket layer, conductive element array, upper pad array, and upper plate together using a clamping mechanism.

In many of these embodiments, the lower pad array is positioned above the lower plate such that a lower pad array bottom is in direct contact with a lower plate top. In many of these embodiments, the gasket layer is positioned above the lower pad array such that a gasket layer bottom is in direct contact with a lower pad array top. In many of these embodiments, the upper pad array is positioned above the gasket layer such that an upper pad array bottom is in direct contact with a gasket layer top. In many of these embodiments, the upper plate is positioned above the upper pad array such that an upper plate bottom is in direct contact with an upper pad array top. In many of these embodiments, the conductive element array is positioned above the lower pad array such that a conductive element array bottom is in direct contact with a lower pad array top.

In many of these embodiments, the conductive element array is positioned below the upper pad array such that a conductive element array top is in direct contact with an upper pad array bottom. In many of these embodiments, the first pattern matches the second pattern such that the conductive element array is aligned with and in conductive contact with the lower pad array. In many of these embodiments, the second pattern matches the third pattern such that the upper pad array is aligned with and in conductive contact with the conductive element array. In many of these embodiments, the clamping mechanism provides a compression force needed to reliably maintain continuous conductive contact between the upper pad array and the lower pad array. In many of these embodiments, the clamping mechanism provides a compression force needed to reliably maintain continuous compression of the gasket layer to electrically isolate each individual vertically connected set of lower pad array element, conductive element, and upper pad array element.

In many of these embodiments, the upper plate and the upper pad array are integrated into a combined upper element. In many of these embodiments, the lower plate and the lower pad array are integrated into a combined lower element. In many of these embodiments, the gasket layer comprises one of a anisotropic conductive elastomer or a compressible dielectric elastic. In many of these embodiments, the clamping mechanism comprises one or more of elastic force generation elements or elastic elements. In many of these embodiments, the force generation elements comprise one or more of a plurality of screws, a plurality of nuts, or a plurality of washers. In many of these embodiments, the elastic elements comprise springs. In many of these embodiments, the plurality of screws pass through the upper plate and end inside the lower plate, and are optionally secured by a plurality of nuts and washers.

In many of these embodiments, the upper pad array comprises a composite of conductive and dielectric materials. In many of these embodiments, the lower pad array comprises a composite of conductive and dielectric materials. In many of these embodiments, the upper plate is rigid. In many of these embodiments, the lower plate is rigid. In many of these embodiments, the lower pad array is one of flexible or rigid.

In many of these embodiments, the lower plate comprises an enclosure and the lower pad array comprises a feedthrough array that enables conductive coupling between an inside of the enclosure, conductive elements in the gasket layer, and the upper pad array. In many of these embodiments, the upper pad array is one of flexible or rigid. In many of these embodiments, one or more of the upper pad array or lower pad array is part of an interface lead that routes electrical traces to one of electrodes or implanted electrodes.

In many of these embodiments, one or more of the upper pad array or lower pad array is part of a lead that routes electrical traces to electronics. In many of these embodiments, one or more of the upper pad array or lower pad array comprises a feed through array that routes electrical signals to electronics inside one of an enclosure or an implanted enclosure. In many of these embodiments, the interface lead is configured to transmit signals to and receive signals from neural tissue or another signal source. In many of these embodiments, the conductive elements comprise one or more of a plurality of micro-fabricated springs, a plurality of metallic micro-particles, or a plurality of metallic micro-wires. In many of these embodiments, the conductive elements are fabricated as an integral part of the lower pad array. In many of these embodiments, the conductive elements are fabricated as an integral part of the upper pad array.

In many of these embodiments, the conductive elements are fabricated as an integral part of the lower pad array and the upper pad array. In many of these embodiments, the conductive elements are fabricated as an integral part of one or more of the feedthrough array or the gasket layer.

In many of these embodiments, the apparatus is configured for disconnecting and reconnecting with a neural interface to change and/or upgrade electronics, or batteries.

In many of these embodiments, the apparatus is configured for implantation in a live subject. In many of these embodiments, the apparatus is configured for one or more of submersion in marine applications, under water deployment, deployment in humid environments, deployment in well drilling or fracking environments, or deployment in environments having harsh or extremely moist conditions.

In many of these embodiments, one or more of the upper plate or lower plate comprises metal, ceramic, glass, or polymer material. In many of these embodiments, the feedthrough array comprises one or more of ceramic, glass, semiconductor, or polymer material. In many of these embodiments, the gasket layer comprises compressible dielectric polymer, silicone, polydimethylsiloxane (PDMS), or polyurethane. In many of these embodiments, one or more of the first pattern, the second pattern, or the third pattern comprises an array pattern.

Conclusion

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:
1. An apparatus, comprising:
   a lower plate;
   a lower pad array comprising a plurality of lower pads, each lower pad arranged in a first pattern and the lower pad array positioned above the lower plate;
   a gasket layer positioned above the lower pad array;
   a conductive element array comprising a plurality of conductive elements, each conductive element arranged in a second pattern, the conductive element array positioned above the lower pad array;

an upper pad array comprising a plurality of upper pads, each upper pad arranged in a third pattern, the upper pad array positioned above the conductive element array;

an upper plate; and a clamping mechanism that enables the lower plate, lower pad array, gasket layer, conductive element array, upper pad array, and upper plate to be compressed together, wherein the plurality of conductive elements are one or more of:

fabricated as an integral part of the lower pad array;

fabricated as an integral part of the upper pad array;

fabricated as an integral part of the gasket layer; or fabricated as an integral part of one or more of a feed through array or the gasket layer.

2. The apparatus of claim 1, wherein one or more of:

the lower pad array is positioned above the lower plate such that a lower pad array bottom is in direct contact with a lower plate top;

the gasket layer is positioned above the lower pad array such that a gasket layer bottom is in direct contact with a lower pad array top;

the upper pad array is positioned above the gasket layer such that an upper pad array bottom is in direct contact with a gasket layer top;

the upper plate is positioned above the upper pad array such that an upper plate bottom is in direct contact with an upper pad array top;

the conductive element array is positioned above the lower pad array such that a conductive element array bottom is in direct contact with a lower pad array top;

the conductive element array is positioned below the upper pad array such that a conductive element array top is in direct contact with an upper pad array bottom;

the first pattern matches the second pattern such that the conductive element array is aligned with and in conductive contact with the lower pad array; or the second pattern matches the third pattern such that the upper pad array is aligned with and in conductive contact with the conductive element array.

3. The apparatus of claim 1, wherein the clamping mechanism provides a compression force needed to reliably maintain one or more of:

continuous conductive contact between each individual vertically connected set of lower pad array element, conductive element, and upper pad array element; or continuous compression of the gasket layer to electrically isolate each individual vertically connected set of lower pad array element, conductive element, and upper pad array element.

4. The apparatus of claim 1, wherein one or more of:

the lower plate and the lower pad array are integrated into a combined lower element; or the upper plate and the upper pad array are integrated into a combined upper element.

5. The apparatus of claim 1, wherein the gasket layer comprises one of an anisotropic conductive elastomer or a compressible dielectric elastic.

6. The apparatus of claim 1, wherein the clamping mechanism comprises one or more of force generation elements or elastic elements.

7. The apparatus of claim 6, wherein the force generation elements comprise one or more of a plurality of screws, a plurality of nuts, or a plurality of washers.

8. The apparatus of claim 6, wherein the elastic elements comprise springs.

9. The apparatus of claim 7, wherein the plurality of screws pass through the upper plate and end inside the lower plate, and are optionally secured by a plurality of nuts and washers.

10. The apparatus of claim 1, wherein one or more of the upper plate or the lower plate is rigid and one or more of the upper pad array or the lower pad array is one of flexible or rigid.

11. The apparatus of claim 1, wherein one of:

the lower plate comprises an enclosure and the lower pad array comprises the feed through array that enables conductive coupling between an inside of the enclosure, conductive elements, and the upper pad array; or the upper plate comprises an enclosure and the upper pad array comprises the feed through array that enables conductive coupling between an inside of the enclosure, conductive elements, and the lower pad array.

12. The apparatus of claim 1, wherein one or more of the upper pad array or lower pad array is part of one or more of:

an interface lead that routes electrical traces to electrodes;

an interface lead that routes electrical traces to implanted electrodes; or a lead that routes electrical traces to electronics.

13. The apparatus of claim 1, wherein one or more of the upper pad array or lower pad array comprises the feed through array that routes electrical signals to electronics inside one of an enclosure or an implanted enclosure.

14. The apparatus of claim 1, wherein the plurality of conductive elements comprise one or more of a plurality of conductive elastic material, springs, micro-fabricated springs, a plurality of metallic micro-particles, a plurality of metallic micro-particles in an elastic material, a plurality of conductive micro-wires, or a plurality of conductive micro-wires in an elastic material.

15. The apparatus of claim 1, configured for one or more of disconnecting and reconnecting with a neural interface to change and/or upgrade electronics or batteries, implantation in a live subject, submersion in marine applications, underwater deployment, deployment in humid environments, deployment in well drilling or fracking environments, or deployment in environments having harsh or extremely moist or electrically conductive conditions.

16. The apparatus of claim 1, wherein one or more of the upper plate or lower plate comprises metal, ceramic, glass, or polymer material.

17. The apparatus of claim 11, wherein the feed through array comprises one or more of ceramic, glass, semiconductor, or polymer material.

18. The apparatus of claim 1, wherein the gasket layer comprises compressible dielectric polymer, silicone, polydimethylsiloxane (PDMS), or polyurethane.

19. A method of manufacturing an apparatus, the method comprising:

positioning a lower pad array above a lower plate, the lower pad array comprising a plurality of lower pads, each lower pad arranged in a first pattern;

positioning a gasket layer above the lower pad array;

positioning a conductive element array above the lower pad array, the conductive element array comprising a plurality of conductive elements, each conductive element arranged in a second pattern;

positioning an upper pad array above the conductive element array, the upper pad array comprising a plurality of upper pads, each upper pad arranged in a third pattern;

positioning an upper plate above the upper pad array; and compressing the lower plate, lower pad array, gasket layer, conductive element array, upper pad array, and upper plate together using a clamping mechanism wherein the plurality of conductive elements are one or more of:
fabricated as an integral part of the lower pad array;
fabricated as an integral part of the upper pad array;
fabricated as an integral part of the gasket layer; or
fabricated as an integral part of one or more of a feed through array or the gasket layer.

* * * * *